US008617542B2

(12) United States Patent
Madhyastha et al.

(10) Patent No.: US 8,617,542 B2
(45) Date of Patent: Dec. 31, 2013

(54) DISPERSINB™, 5-FLUOROURACIL, DEOXYRIBONUCLEASE I AND PROTEINASE K-BASED ANTIBIOFILM COMPOSITIONS AND USES THEREOF

(75) Inventors: Srinivasa Madhyastha, Winnipeg (CA); Purusbottam Gawande, Winnipeg (CA); Karen Lovetri, Winnipeg (CA); Nandadeva Yakandawala, Winnipeg (CA); Jeffrey Kaplan, Monsey, NJ (US)

(73) Assignee: Kane Biotech Inc., Winnipeg (CA)

( * ) Notice: Subject to any disclaimer, the term of this patent is extended or adjusted under 35 U.S.C. 154(b) by 58 days.

(21) Appl. No.: 12/935,982

(22) PCT Filed: Apr. 3, 2009

(86) PCT No.: PCT/CA2009/000430
§ 371 (c)(1),
(2), (4) Date: Dec. 20, 2010

(87) PCT Pub. No.: WO2009/121183
PCT Pub. Date: Oct. 8, 2009

(65) Prior Publication Data
US 2011/0086101 A1 Apr. 14, 2011

Related U.S. Application Data

(60) Provisional application No. 61/041,941, filed on Apr. 3, 2008.

(51) Int. Cl.
*A61K 38/46* (2006.01)
*C12N 9/00* (2006.01)

(52) U.S. Cl.
USPC ........................................ 424/94.65; 435/183

(58) Field of Classification Search
USPC ........................................ 435/183; 424/94.65
See application file for complete search history.

(56) References Cited

U.S. PATENT DOCUMENTS

| | | | |
|---|---|---|---|
| 3,930,000 | A | 12/1975 | Margraf |
| 4,948,575 | A | 8/1990 | Cole et al. |
| 5,197,954 | A | 3/1993 | Cameron |
| 5,238,685 | A | 8/1993 | Wren |
| 5,336,501 | A | 8/1994 | Czech et al. |
| 5,470,576 | A | 11/1995 | Patel |
| 5,482,932 | A | 1/1996 | Thompson |
| 5,674,524 | A | 10/1997 | Scherr |
| 5,735,812 | A | 4/1998 | Hardy |
| 5,738,860 | A | 4/1998 | Schonfeldt et al. |
| 5,908,772 | A * | 6/1999 | Mitta et al. ................ 435/200 |
| 6,700,032 | B1 | 3/2004 | Gray |
| 6,998,509 | B1 | 2/2006 | Nielsen |
| 7,091,336 | B2 | 8/2006 | Cheng et al. |
| 7,294,497 | B2 | 11/2007 | Kaplan |
| 2004/0001878 | A1 | 1/2004 | DeBusk et al. |
| 2005/0035327 | A1 | 2/2005 | Canada et al. |
| 2006/0210613 | A1 | 9/2006 | Carliss |
| 2011/0008402 | A1* | 1/2011 | Madhyastha et al. ......... 424/405 |
| 2011/0311647 | A1 | 12/2011 | Gawande et al. |

FOREIGN PATENT DOCUMENTS

| | | |
|---|---|---|
| WO | 2004061117 | 7/2004 |
| WO | 2005058381 | 6/2005 |
| WO | 2006137847 | 12/2006 |

OTHER PUBLICATIONS

Rohde et al. 2005; Induction of Staphylococcus epidermidis biofilm formation via proteolytic processing of the accumulation-associated protein by staphylococcal and host proteases. Molecular Microbiology. 55(6): 1883-1895.*
Whitchurch et al. 2002; Extracellular DNA retuired for bacterial biofilm formation. Science 295: 1487.*
International Search Report for PCT App. No. PCT/CA2009/000430 mailed on Jul. 14, 2009.
Bates, R. D., et al. "Aerosolized Dornase Alpha (rhDNase) in Cystic Fibrosis," PubMed-NCBI, abstract, J Clin Pharrn Ther. Dec. 1995;20(6): 313-5.
Bennet, G., et al., "The Cost of Pressure Ulcers in the UK," Age and Ageing, vol. 33: No. 3:230-235, British Geriatrics Society (2004).
Brown, L. J., et al., "Periodontal Status in the United States, 1988-1991: Prevalence, Extent, and Demographic Variation," PubMed-NCBI, abstract, J Dent Res. Feb. 1995;75 Spec No: 672-83.
Costerton, J. W., et al., "The Bacterial Glycocalyx in Nature and Disease," Ann. Rev. Microbiol. 1981. 35:299-324.
Costerton, J. W., et al., "Bacterial Biofilms: A Common Cause of Persistent Infections," PubMed-NCBI, abstract, Science. May 21, 1999;284(5418): 1318-22.
Domenico, P., et al., "The Potential of Bismuth-Thiols for Treatment and Prevention of Infection," www.medscape.com/viewarticle/410024, printed Feb. 20, 2013, 5 pages.
Dong, Y., et al., "AiiA, An Enzyme That Inactivates the Acylhomoserine Lactone Quorum-Sensing Signal and Attenuates the Virulence of Erwinia Carotovora," PNAS, Mar. 28, 2000, vol. 97, No. 7:3526-3331.

(Continued)

*Primary Examiner* — Karen Cochrane Carlson
(74) *Attorney, Agent, or Firm* — Whyte Hirschboeck Dudek S.C.

(57) ABSTRACT

The present invention provides antibiofilm composition comprising two or more agents selected from the group consisting of DispersinB™, 5-Fluorouracil, Deoxyribonuclease I and Proteinase K for preventing growth and proliferation of biofilm-embedded microorganisms in wound care, oral care, and disease-related infections and methods of treatment in mammals. The invention further provides methods for preparing medical devices, and wound care devices using an antibiofilm composition comprising two or more antimicrobial agents selected from the group consisting of DispersinB™, 5-Fluorouracil, Deoxyribonuclease I and Proteinase K.

25 Claims, 12 Drawing Sheets

(56) References Cited

OTHER PUBLICATIONS

Donlan, R. M., Biofilms and Device-Associated Infections, Emerging Infectious Diseases, Special Issue, vol. 7, No. 2:277-281, Mar.-Apr. 2001.

Drosou, A., et al., "Antiseptics on Wounds: An Area of Controversy," www.medscape.com/viewarticle/456300, printed Feb. 20, 2013, 27 pages.

Eckhart L, et al., "DNase1L2 Suppresses Biofilm Formation by *Pseudomonas aeruginosa* and *Staphylococcus aureus*," PubMed-NCBI, abstract, Br J Dermatol, Jun. 2007;156(6):1342-5.

Falanga, V., et al., "Workshop on the Pathogenesis of Chronic Wounds," The Society for Investigative Dermatology, Inc.-Meeting Report (1994) 125-127.

Friedberg, E. H., et al., "Current Home Care Expenditures for Persons with Leg Ulcers," PubMed-NCBI, abstract, J Wound Ostomy Continence Nurs. Jul. 2002;29(4): 186-92 Carlson/ (Aug. 19, 2013).

Heyneman, C. A., et al., "Using Hyperbaric Oxygen to Treat Diabetic Foot Ulcers: Safety and Effectiveness," Critical Care Nurse, vol. 22, No. 6:52-60, Dec. 2002.

Izano, E. A., et al., "Poly-N-Acetylglucosamine Mediates Biofilm Formation and Antibiotic Resistance in Actinobacillus Pleuropneumoniae," NIH Public Access, Microb Pathog. Jul. 2007; 43(1):1-17.

Izano, E. A., et al., "Differential Roles of Poly-N-Acetylglocosamine Surface Polysaccharide and Extracellular DNA in *Staphylococcus aureus* and *Staphylococcus epidermidis* Biofilms," Applied and Environmental Microbiology, vol. 74, No. 2:470-476, Jan. 2008.

Jones, M. B., et al., "Inhibition of *Bacillus anthracis* Growth and Virulence-Gene Expression by Inhibitors of Quorum-Sensing," Inhibition of *B. anthracis* Virulence, JID 2005:191 (Jun. 1), 1881-1888.

Kaplan, J. B., "Genes Involved in the Synthesis and Degradation of Matrix Polysaccharide in *Actinobacillus actinomycetemcomitans* and *Actinobacillus pleuropneumoniae* Biofilms," Journal of Bacteriology, Dec. 2004, vol. 186, No. 24:8213-8220.

Longley, D. B., et al., "5-Fluorouracil: Mechanisms of Action and Clinical Strategies," Nature Reviews Cancer 3, 330-338 (May 2003).

March, J. C., et al., "Quorum Sensing and Bacterial Cross-Talk in Biotechnology," Science Direct-Current Opinion in Biotechnology 2004, 15:495-502.

Mertz, P. M., "Feature: Cutaneous Biofilms: Friend or Foe'?," Wounds, printed Feb. 19, 2013, 12 pages.

Moore, W. E. C., "Microbiology of Periodontal Disease," Journal of Periodontal Research, vol. 22, Issue 5:335-341, Sep. 1987.

Munster, A.M., "Treatment of Invasive *Enterobacter cloacae* Burn Wound Sepsis with Topical Nitrofurazone," Health Advance-Record NLM, J Trauma, abstract, 1984; 24:524-5.

Nickel, J. C., et al., "Tobramycin Resistance of *Pseudomonas aeruginosa* Cells Growing As a Biofilm on Urinary Catheter Material," Antimicrobial Agents and Chemotherapy, Apr. 1985, vol. 27, No. 4:619-624.

Petersen, F. C., et al., "Biofilm Mode of Growth of *Streptococcus intermedius* Favored by a Competence-Stimulating Signaling Peptide," Journal of Bacteriology, Sep. 2004, vol. 186, No. 18:6327-6331.

Rasmussen, T. B., et al., "Screening for Quorum-Sensing Inhibitors (QSI) by Use of a Novel Genetic System, The QSI Selector," Journal of Bacteriology, Mar. 2005, vol. 187, No. 5:1799-1814.

Rittenhouse, S., et al., "Use of the Surgical Wound Infection Model to Determine the Efficacious Dosing Regimen of Retapamulin, a Novel Topical Antibiotic," Antimicrobial Agents and Chemotherapy, Nov. 2006, vol. 50, No. 11:3886-3888.

Rohde, H., et al., "Induction of *Staphylococcus epidermidis* Biofilm Formation Via Proteolytic Processing of the Accumulation-Associated Protein by Staphylococcal and Host Proteases," Molecular Microbiology, 55(6), (2005) 1883-1895.

Rothstein, D. M., "Efficacy of Novel Rifamycin Derivatives Against Rifamycin-Sensitive and —Resistant *Staphylococcus aureus* Isolates in Murine Models of Infection," Antimicrobial Agents and Chemotherapy, Nov. 2006, vol. 50, No. 11:3658-3664.

Ruckley, C. V., "Socioeconomic Impact of Chronic Venous Insufficiency and Leg Ulcers," Angiology—The Journal of Vascular Diseases, Jan. 1997, vol. 48, No. 1:67-69.

Sadovskaya, I., et al., "Carbohydrate-Containing Components of Biofilms Produced in Vitro by Some Staphylococcal Strains Related to Orthopaedic Prosthesis Infections," FEMS Immunol Med Microbiol 47 (2006) 75-82.

Strausberg, J., et al., "Pressure Ulcers in Secondary Care: Incidence, Prevalence, and Relevance," PubMed-NCBI, abstract, Adv Skin Wound Care, Apr. 2005; 18(3): 140-5.

Steed, D. L., et al., "Effect of Extensive Debridement and Treatment on the Healing of Diabetic Foot Ulcers. Diabetic Ulcer Study Group," PubMed-NCBI, abstract, J Am Coll Surg. Jul. 1996; 183(1): 61-4.

Tang, J. X., et al., "Anionic Poly (amino acid)s Dissolve F-actin and DNA Bundles, Enhance DNase Activity, and Reduce the Viscosity of Cystic Fibrosis Sputum," Am J Physiol Lung Cell Mol Physiol 289: L599-L5605, (2005).

Travis J., et al., "Are Bacterial Proteinases Pathogenic Factors?," PubMed-NCBI, abstract, Trends Micorbiol. Oct. 1995; 3(10): 405-7.

Whitchurch, C. B., et al., "Extracellular DNA Required for Bacterial Biofilm Formation," PubMed-NCBI, abstract, Science. Feb. 2002; 22; 295(5559): 1487.

Whitchurch, C. B., et al., "Extracellular DNA Required for Bacterial Biofilm Formation," Brevia Microbiology, Science, vol. 295, Feb. 22, 2002.

Wu, H., et al., "Synthetic Furanones Inhibit Quorum-Sensing and Enhance Bacterial Clearance in *Pseudomonas aeruginosa* Lung Infection in Mice," Journal of Antimicrobial Chemotherapy (2004) 53, 1054-1061.

Zaleski, K. J., et al., "Hyaluronic Acid Binding Peptides Prevent Experimental Staphylococcal Wound Infection," Antimicrobial Agents and Chemotherapy, Nov. 2006, vol. 50, No. 11:3856-3860.

Zander, J., et al., "Influence of dTMP on the Phenotypic Appearance and Intracellular Persistence of *Staphylococcus aureus*," Infection and Immunity, Apr. 2008, vol. 76, No. 4:1333-1339.

\* cited by examiner

SEQUENCE LISTING

<160> NUMBER OF SEQ ID NOS: 4

<210> SEQ ID NO 1
<211> LENGTH: 361
<212> TYPE: PRT

<213> ORGANISM: Actinobacillus actinomycetemcomitans

<400> SEQUENCE: 1

```
Asn Cys Cys Val Lys Gly Asn Ser Ile Tyr Pro Gln Lys Thr Ser Thr
1               5                   10                  15
Lys Gln Thr Gly Leu Met Leu Asp Ile Ala Arg His Phe Tyr Ser Pro
            20                  25                  30
Glu Val Ile Lys Ser Phe Ile Asp Thr Ile Ser Leu Ser Gly Gly Asn
        35                  40                  45
Phe Leu His Leu His Phe Ser Asp His Glu Asn Tyr Ala Ile Glu Ser
50                  55                  60
His Leu Leu Asn Gln Arg Ala Glu Asn Ala Val Gln Gly Lys Asp Gly
65                  70                  75                  80
Ile Tyr Ile Asn Pro Tyr Thr Gly Lys Pro Phe Leu Ser Tyr Arg Gln
                85                  90                  95
Leu Asp Asp Ile Lys Ala Tyr Ala Lys Ala Lys Gly Ile Glu Leu Ile
            100                 105                 110
Pro Glu Leu Asp Ser Pro Asn His Met Thr Ala Ile Phe Lys Leu Val
        115                 120                 125
Gln Lys Asp Arg Gly Val Lys Tyr Leu Gln Gly Leu Lys Ser Arg Gln
130                 135                 140
Val Asp Asp Glu Ile Asp Ile Thr Asn Ala Asp Ser Ile Thr Phe Met
145                 150                 155                 160
Gln Ser Leu Met Ser Glu Val Ile Asp Ile Phe Gly Asp Thr Ser Gln
                165                 170                 175
His Phe His Ile Gly Gly Asp Glu Phe Gly Tyr Ser Val Glu Ser Asn
            180                 185                 190
His Glu Phe Ile Thr Tyr Ala Asn Lys Leu Ser Tyr Phe Leu Glu Lys
        195                 200                 205
Lys Gly Leu Lys Thr Arg Met Trp Asn Asp Gly Leu Ile Lys Asn Thr
210                 215                 220
Phe Glu Gln Ile Asn Pro Asn Ile Glu Ile Thr Tyr Trp Ser Tyr Asp
225                 230                 235                 240
Gly Asp Thr Gln Asp Lys Asn Glu Ala Ala Glu Arg Arg Asp Met Arg
                245                 250                 255
Val Ser Leu Pro Glu Leu Leu Ala Lys Gly Phe Thr Val Leu Asn Tyr
            260                 265                 270
Asn Ser Tyr Tyr Leu Tyr Ile Val Pro Lys Ala Ser Pro Thr Phe Ser
        275                 280                 285
Gln Asp Ala Ala Phe Ala Ala Lys Asp Val Ile Lys Asn Trp Asp Leu
290                 295                 300
Gly Val Trp Asp Gly Arg Asn Thr Lys Asn Arg Val Gln Asn Thr His
305                 310                 315                 320
Glu Ile Ala Gly Ala Ala Leu Ser Ile Trp Gly Glu Asp Ala Lys Ala
                325                 330                 335
Leu Lys Asp Glu Thr Ile Gln Lys Asn Thr Lys Ser Leu Leu Glu Ala
            340                 345                 350
Val Ile His Lys Thr Asn Gly Asp Glu
        355                 360
```

<210> SEQ ID NO 2
<211> LENGTH: 282
<212> TYPE: PRT
<213> ORGANISM: Bos taurus

<400> SEQUENCE: 2

```
Met Arg Gly Thr Arg Leu Met Gly Leu Leu Ala Leu Ala Gly Leu
1               5                   10                  15

Leu Gln Leu Gly Leu Ser Leu Lys Ile Ala Ala Phe Asn Ile Arg Thr
            20                  25                  30

Phe Gly Glu Thr Lys Met Ser Asn Ala Thr Leu Ala Ser Tyr Ile Val
        35                  40                  45

Arg Ile Val Arg Arg Tyr Asp Ile Val Leu Ile Gln Glu Val Arg Asp
    50                  55                  60

Ser His Leu Val Ala Val Gly Lys Leu Leu Asp Tyr Leu Asn Gln Asp
65                  70                  75                  80

Asp Pro Asn Thr Tyr His Tyr Val Val Ser Glu Pro Leu Gly Arg Asn
                85                  90                  95

Ser Tyr Lys Glu Arg Tyr Leu Phe Leu Phe Arg Pro Asn Lys Val Ser
            100                 105                 110

Val Leu Asp Thr Tyr Gln Tyr Asp Asp Gly Cys Glu Ser Cys Gly Asn
        115                 120                 125

Asp Ser Phe Ser Arg Glu Pro Ala Val Val Lys Phe Ser Ser His Ser
130                 135                 140

Thr Lys Val Lys Glu Phe Ala Ile Val Ala Leu His Ser Ala Pro Ser
145                 150                 155                 160

Asp Ala Val Ala Glu Ile Asn Ser Leu Tyr Asp Val Tyr Leu Asp Val
                165                 170                 175

Gln Gln Lys Trp His Leu Asn Asp Val Met Leu Met Gly Asp Phe Asn
            180                 185                 190

Ala Asp Cys Ser Tyr Val Thr Ser Ser Gln Trp Ser Ser Ile Arg Leu
        195                 200                 205

Arg Thr Ser Ser Thr Phe Gln Trp Leu Ile Pro Asp Ser Ala Asp Thr
    210                 215                 220

Thr Ala Thr Ser Thr Asn Cys Ala Tyr Asp Arg Ile Val Val Ala Gly
225                 230                 235                 240

Ser Leu Leu Gln Ser Ser Val Val Pro Gly Ser Ala Ala Pro Phe Asp
                245                 250                 255

Phe Gln Ala Ala Tyr Gly Leu Ser Asn Glu Met Ala Leu Ala Ile Ser
            260                 265                 270

Asp His Tyr Pro Val Glu Val Thr Leu Thr
        275                 280

<210> SEQ ID NO 3
<211> LENGTH: 384
<212> TYPE: PRT
<213> ORGANISM: Tritirachium album

<400> SEQUENCE: 3

Met Arg Leu Ser Val Leu Leu Ser Leu Leu Pro Leu Ala Leu Gly Ala
1               5                   10                  15

Pro Ala Val Glu Gln Arg Ser Glu Ala Ala Pro Leu Ile Glu Ala Arg
            20                  25                  30

Gly Glu Met Val Ala Asn Lys Tyr Ile Val Lys Phe Lys Glu Gly Ser
        35                  40                  45

Ala Leu Ser Ala Leu Asp Ala Ala Met Glu Lys Ile Ser Gly Lys Pro
    50                  55                  60

Asp His Val Tyr Lys Asn Val Phe Ser Gly Phe Ala Ala Thr Leu Asp
65                  70                  75                  80

Glu Asn Met Val Arg Val Leu Arg Ala His Pro Asp Val Glu Tyr Ile
                85                  90                  95
```

```
Glu Gln Asp Ala Val Val Thr Ile Asn Ala Ala Gln Thr Asn Ala Pro
            100                 105                 110

Trp Gly Leu Ala Arg Ile Ser Ser Thr Ser Pro Gly Thr Ser Thr Tyr
        115                 120                 125

Tyr Tyr Asp Glu Ser Ala Gly Gln Gly Ser Cys Val Tyr Val Ile Asp
    130                 135                 140

Thr Gly Ile Glu Ala Ser His Pro Glu Phe Glu Gly Arg Ala Gln Met
145                 150                 155                 160

Val Lys Thr Tyr Tyr Ser Ser Arg Asp Gly Asn Gly His Gly Thr
                165                 170                 175

His Cys Ala Gly Thr Val Gly Ser Arg Thr Tyr Gly Val Ala Lys Lys
                180                 185                 190

Thr Gln Leu Phe Gly Val Lys Val Leu Asp Asp Asn Gly Ser Gly Gln
            195                 200                 205

Tyr Ser Thr Ile Ile Ala Gly Met Asp Phe Val Ala Ser Asp Lys Asn
    210                 215                 220

Asn Arg Asn Cys Pro Lys Gly Val Val Ala Ser Leu Ser Leu Gly Gly
225                 230                 235                 240

Gly Tyr Ser Ser Ser Val Asn Ser Ala Ala Ala Arg Leu Gln Ser Ser
                245                 250                 255

Gly Val Met Val Ala Val Ala Ala Gly Asn Asn Asn Ala Asp Ala Arg
            260                 265                 270

Asn Tyr Ser Pro Ala Ser Glu Pro Ser Val Cys Thr Val Gly Ala Ser
    275                 280                 285

Asp Arg Tyr Asp Arg Arg Ser Ser Phe Ser Asn Tyr Gly Ser Val Leu
290                 295                 300

Asp Ile Phe Gly Pro Gly Thr Ser Ile Leu Ser Thr Trp Ile Gly Gly
305                 310                 315                 320

Ser Thr Arg Ser Ile Ser Gly Thr Ser Met Ala Thr Pro His Val Ala
                325                 330                 335

Gly Leu Ala Ala Tyr Leu Met Thr Leu Gly Lys Thr Thr Ala Ala Ser
            340                 345                 350

Ala Cys Arg Tyr Ile Ala Asp Thr Ala Asn Lys Gly Asp Leu Ser Asn
    355                 360                 365

Ile Pro Phe Gly Thr Val Asn Leu Leu Ala Tyr Asn Asn Tyr Gln Ala
370                 375                 380

<210> SEQ ID NO 4
<211> LENGTH: 377
<212> TYPE: PRT
<213> ORGANISM: Actinobacillus pleuropneumoniae

<400> SEQUENCE: 4

Met Lys Lys Ala Ile Thr Leu Phe Thr Leu Leu Cys Ala Val Leu Leu
1               5                   10                  15

Ser Phe Ser Thr Ala Thr Tyr Ala Asn Ala Met Asp Leu Pro Lys Lys
            20                  25                  30

Glu Ser Gly Leu Thr Leu Asp Ile Ala Arg Arg Phe Tyr Thr Val Asp
        35                  40                  45

Thr Ile Lys Gln Phe Ile Asp Thr Ile His Gln Ala Gly Gly Thr Phe
    50                  55                  60

Leu His Leu His Phe Ser Asp His Glu Asn Tyr Ala Leu Glu Ser Ser
65                  70                  75                  80

Tyr Leu Glu Gln Arg Glu Glu Asn Ala Thr Glu Lys Asn Gly Thr Tyr
                85                  90                  95
```

```
Phe Asn Pro Lys Thr Asn Lys Pro Phe Leu Thr Tyr Lys Gln Leu Asn
            100                 105                 110

Glu Ile Ile Tyr Tyr Ala Lys Glu Arg Asn Ile Glu Ile Val Pro Glu
            115                 120                 125

Val Asp Ser Pro Asn His Met Thr Ala Ile Phe Asp Leu Leu Thr Leu
            130                 135                 140

Lys His Gly Lys Glu Tyr Val Lys Gly Leu Lys Ser Pro Tyr Ile Ala
145                 150                 155                 160

Glu Glu Ile Asp Ile Asn Asn Pro Glu Ala Val Glu Val Ile Lys Thr
                165                 170                 175

Leu Ile Gly Glu Val Ile Tyr Ile Phe Gly His Ser Ser Arg His Phe
            180                 185                 190

His Ile Gly Gly Asp Glu Phe Ser Tyr Ala Val Glu Asn Asn His Glu
            195                 200                 205

Phe Ile Arg Tyr Val Asn Thr Leu Asn Asp Phe Ile Asn Ser Lys Gly
            210                 215                 220

Leu Ile Thr Arg Val Trp Asn Asp Gly Leu Ile Lys Asn Asn Leu Ser
225                 230                 235                 240

Glu Leu Asn Lys Asn Ile Glu Ile Thr Tyr Trp Ser Tyr Asp Gly Asp
                245                 250                 255

Ala Gln Ala Lys Glu Asp Ile Gln Tyr Arg Arg Glu Ile Arg Ala Asp
                260                 265                 270

Leu Pro Glu Leu Leu Ala Asn Gly Phe Lys Val Leu Asn Tyr Asn Ser
            275                 280                 285

Tyr Tyr Leu Tyr Phe Val Pro Lys Ser Gly Ser Asn Ile His Asn Asp
            290                 295                 300

Gly Lys Tyr Ala Ala Glu Asp Val Leu Asn Asn Trp Thr Leu Gly Lys
305                 310                 315                 320

Trp Asp Gly Lys Asn Ser Ser Asn His Val Gln Asn Thr Gln Asn Ile
                325                 330                 335

Ile Gly Ser Ser Leu Ser Ile Trp Gly Glu Arg Ser Ser Ala Leu Asn
                340                 345                 350

Glu Gln Thr Ile Gln Gln Ala Ser Lys Asn Leu Leu Lys Ala Val Ile
            355                 360                 365

Gln Lys Thr Asn Asp Pro Lys Ser His
370                 375
```

DISPERSINB™, 5-FLUOROURACIL, DEOXYRIBONUCLEASE I AND PROTEINASE K-BASED ANTIBIOFILM COMPOSITIONS AND USES THEREOF

CROSS REFERENCE TO RELATED APPLICATION

This application claims priority from U.S. Provisional Application No. 61/041,941 filed Apr. 3, 2008, the contents of which are incorporated herein by reference.

FIELD OF THE INVENTION

The present invention relates to antibiofilm compositions comprising two or more antimicrobial agents selected from the group consisting of DispersinB™, 5-Fluorouracil, Deoxyribonuclease I and Proteinase K that inhibit growth and proliferation of biofilm-embedded microorganisms; methods of administering the compositions and methods of treating related disorders.

BACKGROUND

From a microbiological perspective, the primary function of normal, intact skin is to control microbial populations that live on the skin surface and to prevent underlying tissue from becoming colonized and invaded by potential pathogens. Exposure of subcutaneous tissue (i.e. a wound) provides a moist, warm and nutritious environment that is conducive to microbial colonization and proliferation.

Since wound colonization is mostly polymicrobial, involving numerous microorganisms that are potentially pathogenic, any wound is at some risk of becoming infected. In the event of an infection a wound fails to heal, the patient suffers increased trauma as well as increased treatment costs. General wound management practices become more resource demanding. Wounds are an enormous problem worldwide. Approximately 1% of the world's population suffers a venous leg ulcer (Ruckley, 1997. Angiology, 48: 67-69). Friedberg et al. estimated the annual cost for dealing with venous leg ulcers in 192 patients to be $1.26 million (Friedberg et al., 2002. *J. Wound. Ostomy. Continence. Nurs.* 29: 186-192). This equals 6.5 billion of direct wound care cost for every 1 million venous leg ulcer patients. Pressure ulcers are a common and expensive wound care problem in acute care, nursing homes and home care populations. For decubitus ulcer, Stausberg et al. (2005) demonstrated 1% incidence rate along with a 5% prevalence rate for hospital patients (Stausberg et al., 2005. *Adv. Skin Wound. Care,* 18: 140-145). Bennett et al. found that the management of decubitus ulcers costs approximately 3-4 billion dollars annually in the United Kingdom, which is over 4% of the total National Health Service expenditure in the United Kingdom (Bennett et al., 2004. *Ageing,* 33: 230-235). In the United States, diabetic foot ulcers in 2004 consumed approximately 10 billion dollars in direct cost (approximately 4% of the total personal health spending of the United States) and another $5 billion in indirect cost (disability, nursing homes, etc.). Diabetic foot ulcers caused over 100,000 major diabetic limb amputations. The cost for each amputation when factoring in associated costs was $100,000 in 2005, resulting in $10 billion in direct cost (Heyneman and Lawless-Liday, 2002. *Critical Care Nurse,* 22: 52-60). Wounds are becoming an increased portion of the cost of the healthcare system.

Thus, concern among health care practitioners regarding the risk of wound infection is justifiable not only in terms of increased trauma to the patient but also in view of its burden on financial resources and the increasing requirement for cost-effective management within the health care system. Most wound infections are caused by *Staphylococcus aureus* (20%), *Staphylococcus epidermidis* (14%), Enterococci spp. (12%), *Escherichia coli* (8%), *Pseudomonas aeruginosa* (8%), *Enterobacter* spp. (7%), *Proteus* spp. (3%), *Klebsiella pneumoniae* (3%), *Streptococci* (3%) and *Candida albicans* (3%) (CDC Report on common bacterial species associated with wound infections, 1996).

In recent years, there have been numerous efforts to use antibiotics and antimicrobials for the treatment of non-healing, clinically infected wounds. These antimicrobial agents are of varying chemical composition and can include peptides (Zaleski et al., 2006, *Antimicrob. Agents Chemother.,* 50: 3856-3860), antiseptics (U.S. Pat. No. 6,700,032), antibiotics (Rothstein, et al., 2006, *Antimicrob. Agents Chemother.* 50: 3658-3664; Rittenhouse, et al., 2006, *Antimicrob. Agents Chemother.* 50: 3886-3888), silver ions/compounds (US patent appl. pub. no. 2005/0035327), chitosan (US patent appl. pub. no. 2006/0210613; U.S. Pat. No. 6,998,509), nitrofurazone (Munster, 1984, *J. Trauma* 24: 524-525), bismuth thiols (Domenico, et al., 2000, *Infect. Med.* 17: 123-127), and xylitol (WO 2005/058381).

There have been various attempts by others to create wound care devices such as dressings or bandages, gels and ointments comprising antimicrobial agents. For example, U.S. Pat. No. 3,930,000 discloses the use of a silver zinc allantoinate cream for killing bacteria and fungi associated with burn wounds. Another example is silver sulfadiazine (SILVA-DINE®), which has been shown to be effective when tested in vitro against 50 strains of methicillin resistant *S. aureus* (MRSA). Numerous products are commercially available with different trade names that employ silver as antimicrobial agents such as STERIPURE®, A.M.Y., ACTICOAT™, ACTISORB®, and SILVERLON®.

U.S. Pat. No. 7,091,336 teaches the process of making a gel containing gellan gum that increases in viscosity once applied to the wound to form an immobile gel. One example of a commercially available wound gel is INTRASITE®, contains carboxymethyl cellulose as a main ingredient. U.S. Pat. No. 6,700,032 discloses the application of triclosan in wound dressing fabricated from a natural or synthetic film-forming material, such as hydrophobic polymeric membrane. DeBusk and Alleman disclose a wound dressing that has been infused with a suspension of starch hydrolysate containing collagen and α-tocopherol acetate (U.S. patent appl. Pub. No. 2004/0001878). Wounds, in particular those occurring in the skin as second and third degree burns, stasis ulcers, tropic lesions, such as decubitus ulcers, severe cuts and abrasions that are commonly resistant to the natural healing process, may be treated with the infused dressing. Progress has been made on developing wound care devices, but each of the wound etiologies are increasing at double digit rates annually, causing the number of wounds to double every 4-5 years (Drosou et al., 2003, *Wounds,* 15:149-166).

Wounds often have multiple barriers to healing. Wound healing and infection is influenced by the relationship between the ability of bacteria to create a stable, prosperous community within a wound environment and the ability of the host to control the bacterial community. Since bacteria are rapidly able to form their own protective microenvironment (biofilm) following their attachment to a surface, the ability of the host to control these organisms is likely to decrease as the biofilm community matures. Within a stable biofilm community, interactions between aerobic and anaerobic bacteria are likely to increase their net pathogenic effect, enhancing their potential to cause infection and delay healing. Over the last few years, some have linked biofilm to chronic wounds (Mertz, 2003, *Wounds,* 15: 1-9). Microscopic evaluation of chronic wounds showed well organized biofilm with extracellular polymeric substance adhered around colony bacteria in at least 60% of the chronic wounds (Mertz, 2003, *Wounds,* 15: 1-9).

In addition to a direct effect on wound healing by the production of destructive enzymes and toxins, mixed communities of microorganisms may also indirectly affect healing by promoting a chronic inflammatory state. Prolonged exposure to bacteria within a chronic wound leads to a prolonged inflammatory response, resulting in the release of free radicals and numerous lytic enzymes that could have a detrimental effect on cellular processes involved in wound healing. Proteinases released from a number of bacteria, particularly *Pseudomonas aeruginosa*, are known to affect growth factors and many other tissue proteins that are necessary for the wound healing process (Steed et al., 1996, *J. Am. Coll. Surg,* 183: 61-64; Travis et al., 1995, *Trends Microbial.* 3: 405-407). The increased production of exudates that often accompanies increased microbial load has been associated with the degradation of growth factors and matrix metalloproteinases (MMPs), which subsequently affect cell proliferation and wound healing (Falanga et al., 1994, *J Invest Dermatol.* 1: 125-127).

Dental plaque is a host-associated biofilm that adheres to the tooth surface both above and below the gingival margin. Dental plaque consists mainly of microorganisms with a small number of epithelial cells, leukocytes, and macrophages in an intracellular matrix. It has been postulated that there are approximately 300 to 400 different bacterial species in dental plaque (Moore, 1987, *J. Periodont. Res.* 22: 335-341). Periodontal disease comprises a collection of inflammatory conditions of the periodontium (gingiva, periodontal ligament, cementum, and alveolar bone) due to a chronic bacterial infection, i.e., dental plaque. Over 90% of the population of the United States is affected by periodontal disease (Brown et al., 1996, *J. Dent. Res.* 75: 672-683).

In addition to peridontal diseases, other conditions/diseases caused by biofilms include cystic fibrosis pneumonia, native valve endocarditis and otitis media (Costerton et al. Science 1999 284:1318-1322). Biofilm is also implicated in the infection of various medical devices such as urinary catheters, mechanical heart valves, cardiac pacemakers, prosthetic joints, and contact lenses (Donlan, R. M. 2001 Emerging Infect. Dis. 7:277-281). For example, urinary tract infection (UTI) is the most common hospital-acquired infection, accounting for up to 40% of all nosocomial infections. The majority of cases of UTIs are associated with the use of urinary catheters, including trans-urethral foley, suprapubic, and nephrostomy catheters. These urinary catheters are inserted in a variety of populations, including the elderly, stroke victims, spinal cord-injured patients, post-operative patients and those with obstructive uropathy. Despite adherence to sterile guidelines for the insertion and maintenance of urinary catheters, catheter-associated UTIs continue to pose a major problem. For instance, it is estimated that almost one-quarter of hospitalized spinal cord-injured patients develop symptomatic UTIs during their hospital course. Gram-negative bacilli account for almost 60-70%, Enterococci for about 25%, and *Candida* species for about 10% of cases of catheter-associated UTI.

Furthermore, indwelling medical devices including vascular catheters are becoming essential in the management of hospitalized patients by providing venous access. The benefit derived from these catheters as well as other types of medical devices such as peritoneal catheters, cardiovascular devices, orthopedic implants, and other prosthetic devices is often offset by infectious complications. The most common organisms causing these infectious complications are *Staphylococcus epidermidis* and *Staphylococcus aureus*. In the case of vascular catheters, these two organisms account for almost 70-80% of all infectious organisms, with *Staphylococcus epidermidis* being the most common organism. Fungi also form biofilms of clinical significance. *Candida albicans*, a fungal agent, accounts for 10-15% of catheter infections.

Bacteria and fungi growing in biofilms exhibit increased resistance to antimicrobial agents and are nearly impossible to eradicate using known techniques. The present invention teaches applications of a composition comprising two or more antimicrobial agents selected from the group consisting of DispersinB™, 5-Fluorouracil, Deoxyribonuclease I and Proteinase K. Specifically, the present invention teaches uses in medical devices, wound care products, oral care products and methods of treating disease related infections, including those caused by cystic fibrosis. These applications can be for human or animal care.

SUMMARY OF THE INVENTION

The present invention includes compositions and methods for inhibiting growth and formation of biofilms In one embodiment, the present invention provides a composition for preventing and/or inhibiting growth or proliferation of biofilm-embedded microorganisms comprising two or more agents selected from the following group: (a) DispersinB™, (b) 5-Fluorouracil, (c) Deoxyribonuclease I and (d) Proteinase K, or active fragments or variants thereof.

In an embodiment, Dispersin B (DspB) is in a concentration of about 0.5 to about 500 µg/ml. In another embodiment, DspB is in a concentration of about 20 to about 200 µg/ml.

In an embodiment, 5-Fluorouracil (FU) is in a concentration of about 5 to about 500 µg/ml. In a further embodiment, FU is in a concentration of about 10 to about 250 µg/ml.

In an embodiment, Deoxyribonuclease I (DNase I) is in a concentration of about 10 to about 1000 µg/ml. In another embodiment, DNase I is in a concentration of about 100 to about 500 µg/ml.

In an embodiment, Proteinase K (PK) is in a concentration of about 10 to about 1000 µg/ml. In another embodiment, PK is in a concentration of about 100 to about 500 µg/ml.

An embodiment of the invention includes a method of inhibiting proliferation of biofilm-embedded microorganisms comprising administering a therapeutically effective amount of an antibiofilm composition comprising two or more agents selected from: (a) DispersinB™, (b) 5-Fluorouracil, (c) Deoxyribonuclease I and (d) Proteinase K or active fragments or variants thereof.

In another embodiment, the DispersinB™, FU, DNase I and/or PK or active fragments, or variants thereof are administered concurrently.

Another embodiment of the present invention includes a method of treating a disease related infection caused by biofilms comprising administering a therapeutically effective amount of a composition comprised of two or more agents selected from: (a) DispersinB™, (b) 5-Fluorouracil, (c) Deoxyribonuclease I and (d) Proteinase K or active fragments or variants thereof.

A further embodiment of the present invention where the disease related infection can be due to cystic fibrosis.

In yet another embodiment an antibiofilm composition comprising two or more agents selected from (a) DispersinB™, (b) 5-Fluorouracil, (c) Deoxyribonuclease I and (d)

Proteinase K or active fragments or variants thereof, can treat various kinds of wounds, including, but not limited to, cutaneous abscess, surgical wounds, sutured lacerations, contaminated lacerations, burn wounds such as partial and full thickness burns, decubitus ulcers, stasis ulcers, leg ulcers, foot ulcers, venous ulcers, diabetic ulcers, ischemic ulcers, and pressure ulcers.

In a further aspect of the present invention the subject treated can be a mammal.

One embodiment of the present invention includes providing methods of using an antibiofilm composition comprising two or more agents selected from: (a) DispersinB™, (b) 5-Fluorouracil, (c) Deoxyribonuclease I and (d) Proteinase K or active fragments or variants thereof, for manufacture and preparation in wound care devices such as non-resorbable gauze/sponge dressing, hydrophilic wound dressing, occlusive wound dressing, hydrogel wound, and burn dressing. The present invention also includes use of a spray-applicator containing an antibiofilm composition comprising two or more agents selected from: (a) DispersinB™, (b) 5-Fluorouracil, (c) Deoxyribonuclease I and (d) Proteinase K or active fragments or variants thereof, as a wound care device.

An additional aspect of the present invention includes wound care ointments, gels, and lotions comprising an antibiofilm composition comprising two or more agents selected from: (a) DispersinB™, (b) 5-Fluorouracil, (c) Deoxyribonuclease I and (d) Proteinase K or active fragments or variants thereof. An embodiment of the present invention also includes wound care sutures coated with an antibiofilm composition comprising two or more agents selected from: (a) DispersinB™, (b) 5-Fluorouracil, (c) Deoxyribonuclease I and (d) Proteinase K or active fragments or variants thereof.

Furthermore, a composition can comprise binders, wetting agents, odor absorbing agents, levelling agents, adherents, thickeners, and the like. Other additives may be present on and/or within a fabric of bandage including antistatic agents, optical brightening compounds, opacifiers (e.g., titanium dioxide), nucleating agents, antioxidants, UV stabilizers, fillers, permanent press finishes, softeners, lubricants, curing accelerators, adhesives, and the like.

In a further embodiment, gelling agents in a wound gel include, but are not limited to, gums, polysaccharides, alginates, synthetic polymeric compounds, natural polymeric compounds, and mixtures thereof.

In another embodiment, an antibiofilm composition comprising two or more agents selected from: a) DispersinB™, (b) 5-Fluorouracil, (c) Deoxyribonuclease I and (d) Proteinase K or active fragments or variants thereof, can be used to treat an oral infection or disease. Oral infections or diseases include, but are not limited to dental caries; dental plaque; gingivitis; periodontal diseases; mucosal infections (i.e., oral candidiasis, herpes simplex virus infections, recurrent apthlous ulcers etc); oral and pharyngeal cancers; and precancerous legions.

In a further aspect of the present invention the subject treated can be a mammal.

An antibiofilm composition comprising two or more agents selected from: a) DispersinB™, (b) 5-Fluorouracil, (c) Deoxyribonuclease I and (d) Proteinase K or active fragments or variants thereof can be used to inhibit the proliferation of biofilm-embedded gram-negative and gram-positive bacteria, which include, but are not limited to, *Aggregatibacter actinomycetemcomitans*, *Staphylococcus aureus*, *Burkholderia cepacia*, *Escherichia coli*, *Proteus mirabilis*, *Klebsiella pneumoniae*, *Pseudomonas aeruginosa*, *Klebsiella oxytoca*, *Providentia sturtii*, *Serratia marcescens*, *Enterococcus faecalis*, Vancomycin Resistant Enterococci (VRE), *Peptostreptococcus* spp., *Corynebacterium* spp., *Clostridium* spp., *Bacteriodes* spp., *Prevotella* spp., *Streptococcus pyogenes*, *Streptococcus viridans*, *Micrococcus* spp., Beta-hemolytic *streptococcus* (group C), Beta-hemolytic *streptococcus* (group B), *Bacillus* spp., *Porphyromonas* spp., *Enterobacter cloacae*, *S. epidermidis*, *S. aureus*, *Staphylococcus agalactiae*, and *Staphylococcus saprophyticus*.

Additionally, an antibiofilm composition comprising two or more agents selected from: a) DispersinB™, (b) 5-Fluorouracil, (c) Deoxyribonuclease I and (d) Proteinase K or active fragments or variants thereof can also be used to inhibit proliferation of biofilm-embedded fungi, such as *Candida albicans, Candida parapsilosis*, and *Candida utilis*.

Another embodiment, the present invention provides a method of preparing a device comprising treating at least one surface of the device with a composition as herein described. For example, the composition can be incorporated into polymers, wherein said polymers are used to form the device. Another aspect of the present invention is a method of preparing a device comprising coating the composition as herein described onto the inner and/or outer surface of a device.

In one aspect of the present invention, the device is a medical device, such as a catheter, for example, an indwelling catheter such as a central venous catheter, a peripheral intravenous catheter, an arterial catheter, a peritoneal catheter, a haemodialysis catheter, an umbilical catheter, precutaneous nontunneled silicone catheter, a cuffed tunneled central venous catheter, an endotracheal tube, a subcutaneous central venous port, urinary catheter, a peritoneal catheter, a peripheral intravenous catheter or a central venous catheter.

In another embodiment of the present invention, the medical devices are catheters, pacemakers, prosthetic heart valves, prosthetic joints, voice prostheses, contact lenses, a shunt, heart valve, penile implant, small or temporary joint replacement, urinary dilator, cannula, elastomer, or intrauterine devices.

In another embodiment of the present invention, the device is a catheter lock, a needle, a Leur-Lok® connector, a needleless connector, a clamp, a forcep, a scissor, a skin hook, a tubing, a needle, a retractor, a scaler, a drill, a chisel, a rasp, a surgical instrument, a dental instrument, a tube, an intravenous tube, a breathing tube, a dental water line, a dental drain tube, a feeding tube, a bandage, a wound dressing, an orthopedic implant, or a saw.

Another embodiment of the present invention is a method of preparing a device comprising coating a composition herein described onto at least one surface of the device.

Another embodiment of the present invention is a device coated, impregnated, or treated with a composition as herein described, for example, a medical device such as a catheter, for example an indwelling catheter such as a central venous catheter, a peripheral intravenous catheter, an arterial catheter, a peritoneal catheter, a haemodialysis catheter, an umbilical catheter, precutaneous nontunneled silicone catheter, a cuffed tunneled central venous catheter, an endotracheal tube, a urinary catheter, a peritoneal catheter, a peripheral intravenous catheter and central venous catheter or a subcutaneous central venous port.

A device may also be catheters, pacemakers, prosthetic heart valves, prosthetic joints, voice prostheses, contact lenses, a stunt, heart valve, penile implant, small or temporary joint replacement, urinary dilator, cannula, elastomer, intrauterine devices, catheter lock, a needle, a Leur-Lok® connector, a needleless connector, a clamp, a forcep, a scissor, a skin hook, a tubing, a needle, a retractor, a scaler, a drill, a chisel, a rasp, a surgical instrument, a dental instrument, a tube, an intravenous tube, a breathing tube, a dental water line, a dental drain tube, a feeding tube, a bandage, a wound dressing, an orthopedic implant, or a saw.

Another embodiment of the present invention is a method of preventing device or catheter-related infection in a mammal, said method comprising coating, incorporating, or treating a device or catheter to be implanted with a composition as herein described. Another embodiment of the present invention is a method of preventing an infection caused by a device or catheter in a mammal, said method comprising coating, incorporating or treating the device or catheter with a composition as herein described.

Another embodiment of the present invention is the use of a composition as herein described in the preparation of a medical device for implantation in a mammal. In one embodiment, a medical device may be coated, incorporated, or treated with a composition. In another embodiment, the composition may prevent urinary tract infection. Another aspect of the present invention is the use wherein the composition prevents urinary or vascular infection.

DETAILED DESCRIPTION

Definitions

Figure 1:
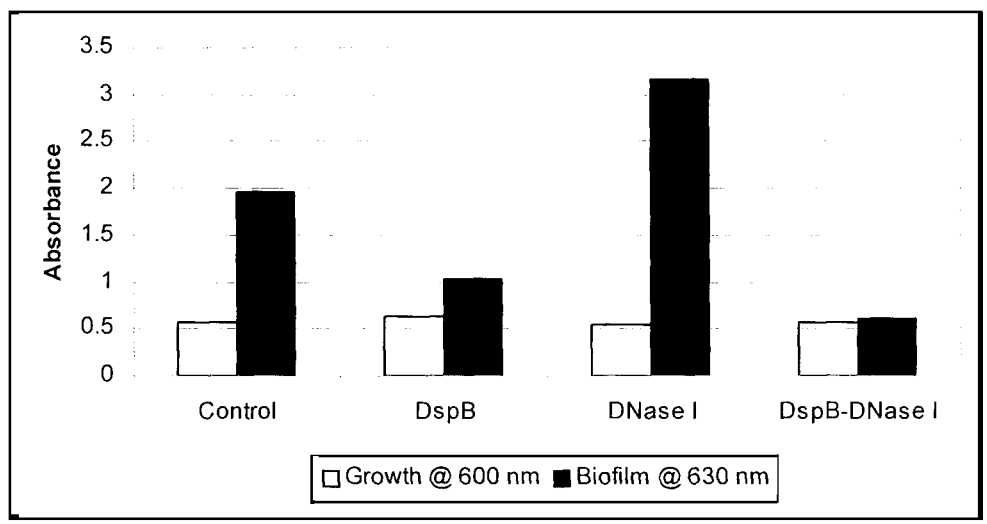
FIG. 1 is a bar graph showing the effect of DispersinB™ (1 µg/ml), and DNaseI (25 µg/ml) on *Staphylococcus epidermis* biofilm formation.

The term "biofilm" as used herein refers to a microbial growth formed by the attachment of microorganisms to surfaces and the subsequent development multiple layers of cells.

The term "DispersinB™" or "DspB" as used herein refers to a protein of SEQ ID NO: 1.

The term "5-Fluorouracil", "FU", "50-fluoro uracil", "5-fluoro-2,4(1H,3H)-Pyrimidinedione", "queroplex", "Ro 2-9757", "Timazin", "U-8953", "Ulup", "5-Fluoro-2,4-pyrimidinedione", "5-Fluoropyrimidine-2,4-dione", "5-Ftouracyl", "5-FU", "Adrucil", "Arumel", "Carzonal", "Effluderm (free base)", "Efudix", "Efudex", "efurix", "Fluoroblastin", "Fluoroplex", "Fluorouracil", "Fluorouracil (Topical)", "Fluracil", "fluracilum", "Fluri", "Fluril", "Fluoroblastin", "ftoruracil" or "Kecimeton" as used herein refer to a compound commonly used for the preparation of a composition used for the treatment of cancer.

The term "Deoxyribonucelase I" or "DNase I" as used herein refers to an enzyme which cleaves phosphodiester bonds, thereby degrading DNA, as can be seen in SEQ ID NO: 2.

The term "Proteinase K", "PK" or "Proteinase K *Tritirachium* album" as used herein refers to an enzyme which cleaves peptide bonds resulting in the degradation of peptides, as can be seen in SEQ ID NO: 3.

The term "active fragment" as used herein are polypeptide sequences structurally different from the DispersinB™, FU, DNase I or PK protein, but having no significant functional difference from the protein.

The term "variant" refers to a polypeptide that contains an amino acid sequence that differs from a wild type or reference sequence. A variant polypeptide can differ from the wild type or reference sequence due to a deletion, insertion, or substitution of a nucleotide(s) relative to said reference or wild type nucleotide sequence. The reference or wild type sequence can be a full-length native polypeptide sequence or any other fragment of a full-length polypeptide sequence. A polypeptide variant generally has at least about 80% amino acid sequence identity with the reference sequence, but may include 85% amino acid sequence identity with the reference sequence, 86% amino acid sequence identity with the reference sequence, 87% amino acid sequence identity with the reference sequence, 88% amino acid sequence identity with the reference sequence, 89% amino acid sequence identity with the reference sequence, 90% amino acid sequence identity with the reference sequence, 91% amino acid sequence identity with the reference sequence, 92% amino acid sequence identity with the reference sequence, 93% amino acid sequence identity with the reference sequence, 94% amino acid sequence identity with the reference sequence, 95% amino acid sequence identity with the reference sequence, 96% amino acid sequence identity with the reference sequence, 97% amino acid sequence identity with the reference sequence, 98% amino acid sequence identity with the reference sequence, 98.5% amino acid sequence identity with the reference sequence, 99% amino acid sequence identity with the reference sequence, or 99.5% amino acid sequence identity with the reference sequence.

The term "therapeutically effective amount" refers to an amount of a composition of this invention effective to "alleviate" or "treat" a disease or disorder in a subject or mammal. A "therapeutically effective amount" as used herein includes a prophylactic amount, for example, an amount effective for preventing or protecting against infectious diseases, and symptoms thereof, and amounts effective for alleviating or treating infectious diseases, related diseases, and symptoms thereof. A "therapeutically effective amount" as used herein also includes an amount that is bacteriostatic or bacteriocidal, for example, an amount effective for inhibiting growth of biofilm associated bacteria or killing biofilm associated bacteria, respectively.

The term "concurrent administration" and "administered concurrently" as used herein includes administering DispersinB™, FU, DNase I and/or PK, active fragments or variants thereof, in a pharmaceutical composition, or as separate compounds, such as, for example, separate pharmaceutical compositions administered consecutively, simultaneously, or at different times.

The term "disease related infection" as used herein refers to an infection which occurs more favourably due to the consequences of the diseased state. For example individuals with cystic fibrosis often are known to have increased mucous secretions in the lungs as well as a compromised immune systems resulting in an increased incidence of pulmonary infections.

The term "wound" as used herein refers to compromised surface integrity of a subcutaneous tissue resulting from trauma, be it accidental or intentional. A wound may be acute or chronic and can include but is not limited to cutaneous abscess, surgical wounds, sutured lacerations, contaminated lacerations, burn wounds such as partial and full thickness burns, decubitus ulcers, stasis ulcers, leg ulcers, foot ulcers, venous ulcers, diabetic ulcers, ischemic ulcers, and pressure ulcers.

The term "wound care device" as used herein refers to materials which are utilized to promote wound healing and aid in the prevention of subsequent infection, and can be non-resorbable gauze/sponge dressing, hydrophilic wound dressing, occlusive wound dressing, hydrogel wound, and burn dressing.

The term "oral infection" or "oral disease" as used herein refers to oral conditions considered to be unhealthy and can be dental caries; dental plaque; gingivitis; periodontal diseases; mucosal infections (i.e., oral candidiasis, herpes simplex virus infections, recurrent apthlous ulcers etc); oral and pharyngeal cancers; and precancerous legions.

The term "biofilm-embedded gram negative bacteria" as used herein refers to microorganisms of a biofilm with gram negative cell walls and can include, but are not limited to *Aggregatibacter actinomycetemcomitans*, *Burkholderia cepacia*, *Escherichia coli*, *Proteus mirabilis*, *Klebsiella pneumoniae*, *Pseudomonas aeruginosa*, *Klebsiella oxytoca*, *Providentia sturtii*, *Serratia marcescens*, *Bacteroides* spp., *Prevotella* spp., *Porphyromonas* spp. and *Enterobacter cloacae*.

The term "biofilm-embedded gram positive bacteria" as used herein refers to microorganisms of a biofilm with gram positive cell walls and can include, but are not limited to *Staphylococcus aureus, Enterococcus faecalis*, Vancomycin Resistant Enterococci (VRE), *Peptostreptococcus* spp., *Corynebacterium* spp., *Clostridium* spp., *Streptococcus pyogenes, Streptococcus viridans, Micrococcus* spp., Beta-hemolytic *streptococcus* (group C), Beta-hemolytic *streptococcus* (group B), *Bacillus* spp., *S. epidermidis, S. aureus, Staphylococcus agalactiae*, and Staphylococcus saprophyticus.

The term "biofilm-embedded fungi" as used herein refers to fungal microorganisms of a biofilm and can include, but are not limited to *Candida albicans, Candida parapsilosis* and *Candida utilis*.

The term "antimicrobial" means a compound or a composition that kills or slows/stops the growth of microorganisms, including, but not limited to bacteria and yeasts, and but not including agents which specifically disperse bacteria or fungi.

A "composition" or "compositions" for use in this invention refers to two or more of DispersinB™, FU, DNase I and/or PK, active fragments or variants thereof that disperses a biofilm, disrupts DNA, cleaves phosphodiester bonds and/or cleaves peptide bonds, optionally in combination with a physiologically acceptable carrier.

The term "detergent" is used to mean any substance that reduces the surface tension of water. A detergent may be a surface active agent that concentrates at oil-water interfaces, exerts emulsifying action and thereby aids in removing soils e.g., common sodium soaps of fatty acids. A detergent may be anionic, cationic, or monionic depending on their mode of chemical action. Detergents include linear alkyl sulfonates (LAS) often aided by "builders." A LAS is preferably an alkyl benzene sulfonate ABS that is readily decomposed by microorganisms (biodegradable). A LAS is generally a straight chain alkyl comprising 10 to 30 carbon atoms. A detergent may be in a liquid or a solid form.

A "viscosity increasing agent", "viscosity improving agent" or "gelling agent" refers to agents that increase viscosity thereby making compositions, such as wound gels, thick and stable. Examples of a viscosity improving agents include, but are not limited to, natural products such as alginic acid, sodium alginate, potassium alginate, ammonium alginate, calcium alginate, agar, carrageenana, locust bean gum, pectin, gelatine, carboxymethyl cellulose (CMC), and chemically synthesized polymers, such as carbopol.

The term "disperse", "dispersion" or "disperse a biofilm" refers to individual bacterial or fungal cells detaching from a surface or detaching from a biofilm. The term "disperse" also refers to disaggregation of autoaggregating bacterial or fungal biofilm cells. "Disperses a biofilm" does not require all biofilm embedded microorganisms to detach, but rather a portion to detach from a surface or a biofilm.

The term "inhibition" or "inhibiting" refers to a decrease of biofilm associated microorganism formation and/or growth. The microorganisms can include bacteria (e.g., streptococci) or fungi (e.g., *Candida* spp.)

The term "modulating detachment" as used herein, is meant to be inclusive of increases as well as decreases in bacterial or fungal biofilm detachment or release of bacterial or fungal cells from a biofilm. Further, "modulating detachment", is also meant to be inclusive of changes in the ability of the bacteria or fungal to attach as a biofilm. For example, as demonstrated herein, DispersinB™ modulates detachment of *S. epiderimidis, Staphylococcus aureus* and *Escherichia coli* not only by promoting detachment but also by inhibiting the ability of the bacteria to attach to surfaces and form a biofilm.

The term "mammal" for purposes of treatment refers to any animal classified as a mammal, including humans, domestic, farm, sport and zoo animals, or pet animals, such as dogs, horses, cats, cattle, pigs, sheep, etc. Preferably, the mammal is human.

The term "treatment", "treating", or "alleviating" refers to an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented.

The term "chronic wound" as defined herein refers to a wound that fails to progress through an orderly and timely sequence of repair or a wound that does not respond to treatment and/or the demands of treatment are beyond the patient's physical health, tolerance or stamina. Many wounds that are first considered to be acute wounds ultimately become chronic wounds due to factors still not well understood. One significant factor is the transition of planktonic bacteria within the wound to form a biofilm.

Methods of Inhibiting Growth and Formation of Biofilms

Agents suitable for use in compositions of the present invention are combined in amounts less than those needed to produce the same antimicrobial effect had the agents been used alone. Each of the agents functions with a unique mechanism to inhibit the growth of bacteria or promote their dispersion from a biofilm.

DispersinB™

Biofilm-embedded *Aggregatibacter* (formerly *Actinobacillus*) *actinomycetemcomitans* can release individual cells into liquid medium. These detached cells can attach to the surface of a culture apparatus and start a new colony. The dspB gene encodes a 381 amino acid soluble β-N-acetylglucosaminidase that is responsible for the detachment/dispersion of *A. actinomycetemcomitans*. This polypeptide is referred to as DispersinB™. The first 20 amino acids are a signal peptide, and amino acids 21-381 are the mature polypeptide. The mature DispersinB™ polypeptide has the following sequence (SEQ ID NO:1; Accession No. AY228551.1):

```
  1nccvkgnsiy pqktstkqtg lmldiarhfy speviksfid tislsggnfl hlhfsdheny

61aieshllnqr aenavqgkdg iyinpytgkp flsyrqlddi kayakakgie lipeldspnh

121mtaifklvqk drgykylqgl ksrqvddeid itnadsitfm qslmsevidi fgdtsqhfhi

181ggdefgysve snhefityan klsyflekkg lktrmwndgl ikntfeqinp nieitywsyd

241gdtqdkneaa errdmrvslp ellakgftvl nynsyylyiv pkasptfsqd aafaakdvik

301nwdlgvwdgr ntknrvqnth eiagaalsiw gedakalkde tiqkntksll eavihktngd

361e
```

The closely related *Actinobacillus pleuropneumoniae* also encodes a DispersinB™, which is a 377 amino acid polypeptide that includes a signal peptide from amino acids 1 to 34. The *A. pleuropneumoniae* DispersinB™ has the following full polypeptide sequence (SEQ ID NO: 4, Accession No. AY618481.1; AAT46094.1 GI:48727581):

```
  1mkkaitlftl lcavllsfst atyanamdlp kkesgltldi arrfytvdti kqfidtihqa

61ggtflhlhfs dhenyaless ylegreenat ekngtyfnpk tnkpfltykq lneiiyyake

121rnieivpevd spnhmtaifd lltlkhgkey vkglkspyia eeidinnpea veviktlige

181viyifghssr hfhiggdefs yavennhefi ryvntlndfi nskglitrvw ndgliknnls

241elnknieity wsydgdaqak ediqyrreir adlpellang fkvlnynsyy lyfvpksgsn

301ihndgkyaae dvlnnwtlgk wdgknssnhv qntqniigss lsiwgerssa lneqtiqqas

361knllkaviqk tndpksh
```

Embodiments of the invention also include active fragments and variants of SEQ ID No: 1 and SEQ ID No: 4. DispersinB™ active fragments and variants only include those fragments and variants that retain an ability to disperse a bacterial or fungal cell from a biofilm.

A substrate for both DispersinB™ is a high-molecular weight hexosamine-containing extracellular polysaccharide adhesin encoded in the pgaABCD locus and pgaCD in *A. acetinomycetemcomitans* and *A. pleuropneumoniae*, respectively (Kaplan et al., 2004, *J. Bacteriol.* 186:8213-8220). These polysaccharide adhesins are a component of the *Aggregatibacter* biofilm. A PGA component of the biofilm functions as a protective barrier for cells of a biofilm. *Aggregatibacter* PGA is structurally and functionally similar to *E. coli* PGA and *S. epidermidis* PIA, both polysaccharides comprising N-acetyl-D-glucosamine residues in a β(1,6) linkage (Kaplan et al., 2004). Thus, embodiments of this invention can be used to detach bacterial cells other than *A. acetinomycetemcomitans* or *A. pleuropneumoniae*. DispersinB™ is fully described in U.S. Pat. No. 7,294,497.

5-Fluorouracil

5-Fluorouracil (FU) is a fluorinated uracil molecule capable of inducing apoptosis and as such is known as a therapeutic cancer drug. FU induces apoptosis by its incorporation into DNA and RNA and its ability to inhibit the activity of thymidylate synthase. FU is able to enter the cell just as uracil can, where it is metabolized to form a variety of compounds namely fluorodeoxyuridine monophosphate, fluorodeoxyuridine diphosphate and fluorodeoxyuridine triphosphate. These compounds cause inhibition of transcription or may be incorporated into newly synthesized RNA (Longley et al. Nat Rev Cancer. 2003 3:330-338). FU has been shown to inhibit the growth of thymidine dependent microbes as they require thymidylate synthase. This can be observed in thymidine dependent small colony variants of *Staphylococcus aureus* of individuals with Cystic Fibrosis (Zander et al. Infect Immun. 2007 Dec. 26 [Epub ahead of print]).

Deoxyribonuclease I

Deoxyribonuclease I (DNase I) is an enzyme which cleaves phosphodiester bonds resulting in the breakdown and destruction of DNA and has been proven to be an effective means in the prevention of biofilm formation and colonization (Eckhart et al., 2007. Br. J. Dermatol. 456(6): 1342-5). The ability of DNase I to depolymerise DNA permits its use in the treatment of bacterial infections, as seen in individuals afflicted with cystic fibrosis (Tang et al., 2005. Am. J. Physiol. Lung. Cell. Mol. Physiol. 289(4): L599-605), said infections being the leading cause of morbidity and mortality (Bates & Nahata, 1995. J. Clin. Pharm. Ther. 20(6): 313-5 (Abstract only)), as well as other instances where infection may be fatal. Izano's recent studies demonstrate the ability of DNase I to inhibit the formation of biofilms caused by *Staphylococcus*

*aureus* and *S. epidermidis*, as well the promotion of *S. aureus* pre-formed biofilm detachment and sensitization of pre-formed *S. aureus* biofilms to detergent degradation (Izano et al., 2007. Appl. Environ. Microbiol. 2007 Nov. 26 [Epub ahead of print]).

The anatomy of a biofilm is somewhat complex, where single-celled microorganisms communicate through methods of quorum sensing to allow the growth of a biofilm, sometimes less formally referred to as "multicellular" due to the cooperative relationship of the cells in question. Investigators have been attempting to determine the degree of necessity of extracellular DNA in the formation of biofilms. The matrix of a given biofilm is comprised of a variety of molecules, one of which being DNA. While some originally believed that this DNA was present due to cellular lysis, it now appears that with specific regard to gram negative microorganisms this DNA is present due to the release of vesicles from the outer membrane as can be seen with the formation of *Pseudomonas aeruginosa* biofilms. Gram positive species such as *Streptococcus intermedius* are still believed to exhibit extracellular DNA in the biofilm matris due to cellular lysis, thereby liberating the DNA (Petersen et al. J. Bacteriol. 2004. 186(18): 6327-6331). The importance of this DNA can be determined by a simple assay where the presence of DNase I in the culture medium inhibited biofilm formation by *Pseudomonas aeruginosa* (Whitchurch et al. Science. 2002. 295: 1487) and *Streptococcus intermedius* (Petersen et al. J. Bacteriol. 2004. 186(18): 6327-6331), thus the extracellular DNA is required for the establishment of the biofilm itself.

Proteinase K

Proteinase K (PK) is a protease which cleaves peptide bonds. PK is known to promote dispersion of bacterial biofilms comprised of microorganisms which do not produce detectable amounts of poly-$\beta$-(1→6)-N-acetyl-D-glucosamine (PNAG) (carbohydrate moiety possessed by certain biofilm forming microorganisms) while those which do produce PNAG are dispersed by the actions of DispersinB™. A variety of *S. aureus* and *S. epidermidis* strains are susceptible to dispersion by PK (Sadovskaya et al. 2006. FEMS Immunol. Med. Microbiol. 47(1): 75-82). This is further confirmed by studies with *Aggregatibacter actinomycetemcomitans*. *A. actinomycetemcomitans* produces PNAG which is genetically quite similar to the PNAG produced by *S. aureus*, *S. epidermidis* and *E. coli*. Disruption/deletion of the genes within the operon encoding PNAG results in susceptibility of said biofilm to dispersion/detachment by Proteinase K when these cells have been pretreated with DispersinB™ (Izano et al. 2007. Microb. Pathog. 2007 Aug. 12 [Epub ahead of print]).

The composition disclosed herein is an effective means to inhibit growth and proliferation of biofilm-embedded microorganisms due to its ability to produce its effects on microorganisms which express PNAG as well as those which do not express PNAG, and any microorganisms whose biofilm matrix includes DNA (including gram positive and gram negative microbes).

Compositions for Inhibiting Growth and Formation of Biofilms

Antibiofilm enzyme-based antimicrobial compositions comprising two or more of DispersinB™, 5-Fluorouracil, Deoxyribonuclease I and Proteinase K' or active fragments or variants thereof, can inhibit biofilm formation as well as biofilm growth. Such compounds are effective for inhibiting growth and proliferation of biofilm-embedded microorganisms, including both bacterial and fungal species. An enhanced antimicrobial activity of any two or more of DNase I, FU, PK, and DispersinB™ is evidenced by the low concentration of each compound required to inhibit bacterial growth effectively.

It will be appreciated that compositions comprising two or more of DispersinB™, 5-Fluorouracil, Deoxyribonuclease I and Proteinase K, or active fragments or variants thereof can be used together in the form of a single composition in one embodiment or together in the form of separate compositions for inhibiting growth and proliferation of biofilm-embedded microorganisms in another embodiment. In embodiments wherein separate compositions comprising DispersinB™, 5-Fluorouracil, Deoxyribonuclease I or Proteinase K, or active fragments or variants thereof and antimicrobial agents are employed, the separate compositions can be used at the same time or sequentially. In a preferred embodiment, a composition comprising DispersinB™ or an active fragment or variant thereof is administered separately to a biofilm to be treated followed by separate administration of a composition comprising 5-Fluorouracil, Deoxyribonuclease I and/or Proteinase K, for inhibiting growth and proliferation of biofilm-embedded microorganisms.

Accordingly, an embodiment of the present invention provides compositions for preventing growth and proliferation of biofilm embedded-microorganisms comprising: two or more of DispersinB™, 5-Fluorouracil, Deoxyribonuclease I and Proteinase K, active fragments, or variants thereof.

An enhanced antimicrobial composition of the invention requires remarkably small amounts of active ingredients (compared to that used in the past) to be effective against the microbial growth and biofilm formation. A composition according to the invention may have properties that include those of separate compounds but go beyond them in efficacy and scope of application. Extremely low levels, and hence increased efficacy, of active compounds or ingredients, make embodiments of this invention very desirable and relatively economical to manufacture, although higher concentrations of these compounds can be used if it is desired for certain applications. A further advantage of using these compositions is the effectiveness for preventing growth of biofilm embedded bacteria and fungus, and in particular, bacterial and fungal species that colonize wounds.

Antimicrobial compositions of the invention can be used to inhibit the proliferation of biofilm-embedded gram-negative and gram-positive bacteria, which include, but are not limited to: *Escherichia coli, Proteus mirabilis, Klebsiella pneumoniae, Pseudomonas aeruginosa, Klebsiella oxytoca, Providentia stuartii, Serratia marcescens, Enterococcus faecalis,* Vancomycin Resistant Enterococci (VRE), *Peptostreptococcus* spp., *Corynebacterium* spp., *Clostridium* spp., *Bacteroides* spp., *Prevotella* spp., *Streptococcus pyogenes, Streptococcus viridans, Micrococcus* spp., $\beta$-hemolytic *streptococcus* (group C), Beta-hemolytic *streptococcus* (group B), *Bacillus* spp., *Porphyromonas* spp., *Aggregatibacter actinomycetemcomitans, Fusobacterium nucleatum, Treponema denticola, Staphylococcus epidermidis, Staphylococcus aureus* and *Staphylococcus saprophyticus*.

Additionally, antimicrobial compositions of the invention can also be used to inhibit the proliferation of biofilm-embedded fungi, such as *Candida albicans, Candida parapsilosis,* and *Candida utilis*.

In one aspect, the antimicrobial compositions can treat various kinds of wounds, including, but not limited to, cutaneous abscesses, surgical wounds, sutured lacerations, contaminated lacerations, blister wounds, soft tissue wounds, partial thickness and full thickness burns, decubitus ulcers, stasis ulcers, leg ulcers, foot ulcers, venous ulcers, diabetic ulcers, ischemic ulcers, and pressure ulcers.

Another aspect includes methods of using the antimicrobial compositions in wound care devices including, but not limited to, non-resorbable gauze/sponge dressing, hydrophilic wound dressing, occlusive wound dressing, hydrogel wound and burn dressing, spray-applicator, and also in ointments, lotions, and suture.

Suitable substrates for receiving a topically applied antimicrobial composition finish include, without limitation, fibres, fabrics, and alginates. A fabric may be formed from fibres such as synthetic fibres, natural fibres, or a combination thereof. Synthetic fibres include, for example, polyester, acrylic, polyamide, polyolefin, polyaramid, polyurethane, regenerated cellulose (i.e., rayon), and blends thereof. Suitable polymeric materials include but are not limited to silastic or other silicone-based material, polyethylenetecephtalate (PET), Dacron®, knitted Dacron®, velour Dacron®, polyglacin, chromic gut, nylon, silk, bovine arterial graft, polyethylene (PE), polyurethane, polyvinyl chlorides silastic elastomer, silicone rubber, PMMA [poly-(methylmethacrylate), latex, polypropylene (PP), polyolefin, cellulose, poly vinyl]alcohol (PVA), poly(hydroxyethyl methacrylate (PHEMA), poly(glycolic acid), poly (acrylonitrate) (PAN), fluoroethylene-cohexa-fluoropropylene (FEP), Teflon® (PTFE), Cobalt-Cromium alloys, copolymers thereof and mixtures thereof.

A method of incorporating the therapeutically active compositions of the present invention into the polymeric material includes direct compounding of a therapeutically active substance into a plastic resin before casting or the like.

In addition, the antimicrobial compositions can further comprise binders, wetting agents, odour absorbing agents, levelling agents, adherents, thickeners, and the like. Other additives may also be present on and/or within a fabric of bandage including antistatic agents, optical brightening compounds, opacifiers (such as titanium dioxide), nucleating agents, antioxidants, UV stabilizers, fillers, permanent press finishes, softeners, lubricants, curing accelerators, adhesives, and the like.

In another embodiment, the antimicrobial compositions can include a detergent. A detergent may be anionic, cationic, or non-ionic. Detergents can include: sodium dodecyl sulfate (SDS) (also known as lauryl sulfate, sodium salt (other salts are also useful including lithium and potassium salts); sodium cocomonoglyceride sulfonate; sodium lauryl sarcosinate; sodium cholate; sodium deoxycholate; octylglucoside; dodecyldimethylamine oxide; 3-[(3-cholamidopropyl)dimethylammonio]-1-propanesulfonate (CHAPS); dodecyltriethylammonium bromide (DTAB); cetyltrimethylammonium bromide (CTAB); polyoxyethylene-p-isooctylphenyl ether (e.g., Triton® X-20, Triton® X-100, Triton® X-114); alkyl sulfate; alkyl sulfonate; quaternary amines; octyldecyldimethylammonium chloride; dioctyldimethylammonium chloride; didecyldimethylammonium chloride; cetylpyridinium chloride; benzalkonium chloride; benzyldodecyldimethylammonium bromide; thonzonium bromide; cholic acid; chenodeoxycholic acid; glycodeoxychlic acid sodium salt; cremophor EL; N-Nonanoyl-N-methylglucamine; saponin; surfactin; protamine, and colistin.

In another embodiment, the antimicrobial compositions can also include photosensitive drugs including but not limited to methylene blue, nuclear Fast Red, delta-aminolaevulinic acid, phenothiazine chloride, tetra(N-methyl-4-pyridyl)porphine tetratosylate salt (TMPyP), toluidine blue O (TBO), methylene blue trihydrate (MB), Photolon, protoporhyrin PPIX, merocyanine 540, photofrin, aluminum phthalocyanine chloride.

Therapeutic Use for Treating Oral Infections

In an embodiment, the antimicrobial compositions can treat an oral infection. Oral infections include microorganisms in the subgingival and supragingival plaque. Subgingival plaque comprises microorganisms can cause periodontal disease. Periodontal disease includes gingivitis, periodontitis, acute necrotizing ulcerative gingivitis (ANUG), and localized juvenile periodontitis (LJP). Symptoms of periodontal disease include inflammation of the gingiva, deepening periodontal pockets, and alveolar bone loss.

*A. actinomycetemcomitans* is the principal etiologic agent of LJP and is considered a putative etiologic agent for generalized periodontitis, also referred to as adult periodontitis. *Prevotella intermedia* is considered the chief etiologic agent for ANUG and is also considered a putative etiologic agent of adult periodontitis. *Porphyromonas gingivalis* is considered the main etiologic agent of chronic and severe adult periodontitis, but other microorganisms are thought to contribute to adult periodontitis as well. Other etiologic agents of periodontal diseases include *Fusobacterium nucleatum, Treponema denticola, Eikenella corrodens, P. nigrescens, Campylobacter rectus*, and *Bacteroides forsythus*.

In an embodiment, the compositions can be used to treat oral infections. Preferably, an oral infection would include dental plaque that causes periodontal disease. In another embodiment, an oral infection includes *Streptococcus mutans*, the etiologic agent of caries.

In an embodiment, a method includes administering a composition comprising two or more of DispersinB™, 5-Fluorouracil, Deoxyribonuclease I and Proteinase K, active fragments or variants thereof that disperses a biofilm, cleaves phosphodiester bonds and/or cleaves peptide bonds.

A structural matrix established during biofilm formation can make colonizing cells able to withstand normal treatment doses of an antimicrobial. In a biofilm, a glycocalyx matrix serves as a barrier that protects and isolates microorganisms from antimicrobials and host defenses (e.g., antibodies, macrophages, etc.) (Costerton et al., 1981, *Ann. Rev. Microbiol.* 35:299-324). In one study, biofilm-associated bacteria were able to survive a concentration of antibiotic 20 times the concentration effective to eliminate the same species of bacteria grown in planktonic culture (Nickel et al., 1985, *Antimicrob. Agents Chemother.* 27:619-624). Higher doses of antimicrobials necessary to eliminate biofilm growth may not be well tolerated in a mammal, particularly a human. The composition can overcome this structural protection of biofilm-embedded microorganisms. DispersinB™ can break up a biofilm matrix, whereby FU, DNase I and PK then have access to the microorganisms.

Therapeutic Use for Treating Cystic Fibrosis Related Infections

In an embodiment, the antimicrobial compositions can treat disease-related infections. Disease-related infections may be due affliction with Cystic Fibrosis. Cystic Fibrosis patients often have increased mucous within the lungs and a compromised immune system resulting in increased incidence of infection.

Microorganisms commonly associated with infections subsequent to Cystic Fibrosis include, but are not limited to *Burkholderia cepacia, Pseudomonas aeruginosa, Staphylococcus aureus, Haemophilus influenzae, Stenotrophomonas maltophilia, Alcaligenes xiloxidants, Mycobacterium avium* and *Mycobacterium abscessus*.

In an embodiment, a method includes administering a composition comprising two or more of DispersinB™, 5-Fluorouracil, Deoxyribonuclease I and Proteinase K, active fragments or variants thereof that disperses a biofilm, cleaves phosphodiester bonds and/or cleaves peptide bonds.

The composition can overcome the structural protection of biofilm-embedded microorganisms as previously described herein. DispersinB™ can break up a biofilm matrix, whereby FU, DNase I and PK then have access to the microorganisms.

Gel Formulations

In another embodiment, the present invention provides antibiofilm enzyme-based wound gel compositions comprised of two or more of DispersinB™, 5-Fluorouracil, Deoxyribonuclease I and Proteinase K, or active fragments or variants thereof, can inhibit biofilm formation as well as biofilm growth. In particular, a composition can include any two or more of DispersinB™, 5-Fluorouracil, Deoxyribonuclease I and Proteinase K. Such compositions are effective in inhibiting growth and proliferation of biofilm-embedded microorganisms, including both bacterial and fungal species. A composition can further comprise a viscosity improving agent.

Accordingly, an embodiment of the present invention provides wound gel compositions for: two or more of DispersinB™, 5-Fluorouracil, Deoxyribonuclease I and Proteinase K antimicrobial wound gel with a viscosity improving agent (gelling agent). In the wound gels two or more of DispersinB™, 5-Fluorouracil, Deoxyribonuclease I and Proteinase K or active fragments or variants thereof could be used.

An antibiofilm composition comprising two or more antimicrobial agents selected from the group consisting of DispersinB™, 5-Fluorouracil, Deoxyribonuclease I and Proteinase K wound gel can be prepared in polyethylene glycol (PEG)/ethanol. PEG of molecular weights ranging between 200 and 511000 can be used in the gel formulation. According to another embodiment, the wound gel is prepared in 10% polyethylene glycol (PEG) 400 plus 10% ethanol.

According to another embodiment, a viscosity increasing agent is an alginate based material. There are a number of suitable viscosity increasing agents available and, as previously indicated, preferred embodiments of the present invention will rely on gelling agents. A number of gelling agents are available including various gums and polysaccharides, alginates, and both synthetic and natural polymeric compounds. Such gelling agents are well known in the art, in particular in the food and medical arenas and will not be discussed in any specific detail herein apart from some representative examples given later herein. Some useful prior art referencing the use of gelling agents in medical type applications include U.S. Pat. No. 4,948,575, U.S. Pat. No. 5,674,524, U.S. Pat. No. 5,197,954, U.S. Pat. No. 5,735,812, U.S. Pat. No. 5,238,685, U.S. Pat. No. 5,470,576, U.S. Pat. No. 5,738,860, U.S. Pat. No. 5,336,501, U.S. Pat. No. 5,482,932. Reference is made to these documents as a background to various viscosity increasing agents, which may find with the present invention.

Two or more of DispersinB™, 5-Fluorouracil, Deoxyribonuclease I and Proteinase K based antimicrobial wound gel can be used to inhibit the proliferation of biofilm-embedded gram-negative and gram-positive bacteria, which include, but are limited to: *Escherichia coli, Proteus mirabilis, Klebsiella pneumoniae, Pseudomonas aeruginosa, Klebsiella oxytoca, Providentia sturtii, Seratia marcescens, Enterobacter cloacae, Enterococcus faecalis*, Vancomycin Resistant Enterococci (VRE), *Peptostreptococcus* spp., *Corynebacterium* spp., *Clostridium* spp., *Bacteriodes* spp., *Prevotella* spp., *Streptococcus pyogenes, Streptococcus* viridans, *Micrococcus* spp., Beta-hemolytic *streptococcus* (groupC), Beta-hemolytic *streptococcus* (groupB), *Bacillus* spp., *Porphyromonas* spp., *Staphylococcus epidermidis, S. aureus, S. agalactiae* and *S. saprophyticus*.

Additionally, two or more of DispersinB™, 5-Fluorouracil, Deoxyribonuclease I and Proteinase K based antimicrobial composition can also be used to inhibit the proliferation of biofilm-embedded fungi, such as *Candida albicans, Candida parapsilosis*, and *Candida utilis*.

Use of Gel Formulations

An antibiofilm composition comprising two or more antimicrobial agents selected from the group consisting of DispersinB™, 5-Fluorouracil, Deoxyribonuclease I and Proteinase K based antibiofilm gel formulations can be administered to subjects to inhibit biofilms. Such biofilms can include bacteria, fungi, or a mixture of bacteria and fungi. Biofilms can be associated with wounds. Administration of two or more of DispersinB™, 5-Fluorouracil, Deoxyribonuclease I and Proteinase K based antibiofilm wound gel can also be achieved wherein a wound dressing or device comprises said two or more of DispersinB™ 5-Fluorouracil, Deoxyribonuclease I and Proteinase K based antibiofilm gel formulations.

In one aspect, an antibiofilm composition comprising two or more antimicrobial agents selected from the group consisting of DispersinB™, 5-Fluorouracil, Deoxyribonuclease I and Proteinase K based antibiofilm wound gel can be used for treating wounds that includes but is not limited to, a cutaneous abscess, surgical wound, sutured laceration, contaminated laceration, blister wound, soft tissue wound, partial thickness burn, full thickness burn, decubitus ulcer, stasis ulcer, foot ulcer, venous ulcer, diabetic ulcer, ischemic ulcer, pressure ulcer, or combinations thereof.

A wound gel is preferably applied following wound debridement. Although biofilm bacteria cannot be completely eradicated from a wound area by debridement, decreasing biofilm mass and providing increased exposure of the debrided tissue and remaining biofilm bacteria to a wound gel increases wound healing. The slough that fills a chronic wound, previously thought to be comprised of dead cells, cellular debris, bacteria, and tissue fluid, has recently been demonstrated to be comprised primarily of a mixed-species bacterial biofilm. It is therefore of benefit to debride the slough from the wound as completely as possible. Debridement can be performed by surgical, mechanical, autolytic, enzymatic, or a combination of means known to those of skill in the art of wound care.

A wound gel could be applied on chronic wounds along with systemic administration of antibiotics. At present antibiotics are not effective against some chronic wounds as biofilm embedded cells are more resistant to antibiotics. Application of a wound gel with antibiofilm activity will disrupt biofilm embedded cells and systemically administered antibiotics will kill dispersed cells. Therefore, a wound gel of present invention will improve the activity of antibiotics.

A wound gel of the present invention utilizes alginate salts to form a product of the desired viscosity (e.g. gel, putty or pliable sheet, etc.). Alginates appear to be especially suitable for use with a wound gel since physical properties of a gel product appear to be relatively easily controlled. Introduction of polyvalent cations helps to form a gel product of desired consistency. Any moulding, extruding, or forming processes should also be performed at this time so that a final product could be formed into desired configuration. Machining (e.g. slicing) into a final form, such as sheets cut from a block, can also be incorporated into any manufacturing process.

Alginates can also have other potentially realisable advantages by introducing cations or cations that are already a part of the selected alginate. For instance, calcium containing alginates may be selected where there is bleeding, as calcium can promote blood clotting. Another example of advantageous cation exchange by an alginate includes alginate fibre dressings that are high in mannuronic acid, wherein the fibre dressings can readily exchange calcium ions for sodium ions. This increases fluid uptake by the dressing, which consequently forms a soft gel that can be easily flushed away with saline. Fibre dressings high in guluronic acid form stronger gels that keep their shape, making removal in one piece possible.

Alginates can exhibit gelling and cross linking properties promoted by the presence of polyvalent cations. These often tend to form tougher and less soluble alginate materials and thus may find use in a number of products for altering physical characteristics. Such a modification can be used for a sheet-like embodiment, particularly as a way of increasing the strength or solubility properties of a resulting sheet.

Polyvalent cations may be introduced in a number of ways, including introduction of a soluble solution of polyvalent cations during the blending procedure. Preferably, this should be after gelling of a blend has been initiated to avoid thickening reactions, which interfere with the dispersion and hydrating of all of the sodium (or other) alginate being blended with two or more of DispersinB™, 5-Fluorouracil, Deoxyribonuclease I and Proteinase K. However, adding polyvalent cations at different points can theoretically substantially alter the characteristics of the resulting product and thus a number of options open to the user to allow them to tailor the physical characteristics of products according to the intended end use and user requirements. It is anticipated that soluble calcium salts, such as calcium chloride, may be introduced at relatively low concentrations to promote the various gelling and cross reactions.

Sheets from wound gels can be formed by placing wound gel in between sheets of a non-wettable material and rolling it to uniform thickness. As a variation, a gauze fabric or other suitable material may be placed on top of a lower non-wettable sheet prior to pouring a wound gel. The rolling procedure is completed with a sheet-like gel bonded to gauze. Various materials could be used to apply two or more of DispersinB™, 5-Fluorouracil, Deoxyribonuclease I and Proteinase K based wound gel including, without limitations, fibres, and fabrics. A fabric may be formed from fibres such as synthetic fibres, natural fibres, or combinations thereof. Synthetic fibres include, for example, polyester, acrylic, polyamide, polyolefin, polyaramid, polyurethane, regenerated cellulose (i.e. rayon), and blends thereof. Suitable polymeric materials include but are not limited to silastic or other silicone-based material, polyethylenetecephtalate (PET), Dacron®, kitted Dacron®, velour Dacron®, polyglacin, chromic gut, nylon, silk, bovine arterial graft, polyethylene (PE), polyurethane, polyvinyl chlorides silastic elastomer, silicone rubber, PMMA[poly-(methylmethacrylate), latex, polypropylene (PP), polyolefin, cellulose, poly vinyl]alcohol (PVA), poly(hydroxymethyl)methacrylate (PHEMA), Poly (glycolic acid), poly(acrylonitrate) (PAN), fluoroethylenecohexa-fluoropropylene (FEP), Teflon® (PTFE), Cobalt-Cromium alloys, copolymers thereof and mixtures thereof.

Other potentially useful gelling agents include hydrocolloids and hydrogels. These components tend to absorb moisture to form a moist healing environment and tend to absorb less fluid than the alginates. Consequently it is envisaged that they would not be used for embodiments for heavily exuding wounds in which alginates would tend to offer better performance. However, it is envisaged that combinations of various viscosity increasing agents may be used in particular embodiments, particularly each imparts a slightly different property which helps fulfil a particular specification required by the user. For instance the hydrocolloids or hydrogels may be incorporated into gelling blends to vary properties such as the amount of fluid absorbed from a wound, etc.

In addition, an antibiofilm composition comprising two or more antimicrobial agents selected from the group consisting of DispersinB™, 5-Fluorouracil, Deoxyribonuclease I and Proteinase K based wound gels can further comprise binders, wetting agents, odour absorbing agents, levelling agents, adherents, thickeners, coupling agents, pH adjusters, and the like.

A formulation of the present invention may be used for human wound therapy or for veterinary use. A formulation may be applied topically to one or more wounds of, for example, a dog, cat, or other mammal. A formulation may be applied to a bite wound to protect a human from developing an ulcerated wound as the result of infection (often with biofilm fragments from the mouth of the animal).

Compositions of the invention can also include quorum sensing inhibitors (QSIs). Quorum sensing is a means of communication between bacteria, most notably in a biofilm. Quorom sensing is mediated by N-acyl-homoserine lactones (AHLs) in gram-negative bacteria and mostly through small peptides in gram positive bacteria (March & Bentley, *Curr. Opin. Biotechnol.* 15: 495-502 (2004)). Quorom sensing inhibitors can inhibit AHL expression, dissemination, and signal reception. For instance, the *Bacillus* enzyme AiiA hydrolyzes AHLs (Dong et al., *Proc. Natl. Acad. Sci. USA* 97: 3526-3531 (2000)). Other QSIs can include AHL analogs that compete and/or interfere with AHL binding to a receptor (e.g., LuxR). These antagoinst AHLs can include AHLs with a longer acyl side chains (e.g., extended with at least one methylene), AHLs with decreased acyl side chain rotation (e.g., introduction of an unsaturated bond close to the amide linkage), or a substitution to the phenyl ring (e.g., para-bromo). Other QSIs include furanone compounds (Wu et al., *J. Antimicrob. Chemother.* 53: 1054-1061 (2004)) such as (5Z)-4-bromo-5-(bromomethylene)-3-butyl-2(5H)-furanone (Jones et al., *J. Infect. Dis.* 191: 1881-1888 (2005)), 4-nitropyridine-N-oxide, garlic extract, p-benzoquinone, 2,4,5-tribromo-imidazole, 3-amino-benzen-sulfonamide, and 3-nitro-benzen-sulfonamide (Rasmussen et al., *J. Bacteriol.* 187: 1799-1814 (2005)).

Methods to modulate biofilm detachment can include an antibiofilm composition comprising two or more antimicrobial agents selected from the group consisting of DispersinB™, Deoxyribonuclease I and Proteinase K and other molecules mentioned above. Any two or more of DispersinB™, 5-Fluorouracil, Deoxyribonuclease I and Proteinase K can be administered to a biofilm concurrently or prior to administering QSIs and/or an antimicrobial. Further, any two or more of DispersinB™, 5-Fluorouracil, Deoxyribonuclease I and Proteinase K and QSIs can be administered concurrently or prior to administering an antimicrobial.

Treatment of Devices

In a further embodiment, a composition(s) of the present invention can be used to inhibit the growth and proliferation of biofilm embedded microorganisms on devices, and in particular, medical devices. The compositions of the present invention can be used in the preparation of medical devices for implantation in a mammal. A medical device to be implanted can be coated, incorporated or treated with a composition(s) of the present invention. A composition(s) of the present invention can also be used to prevent infections caused by an implanted medical device, including but not limited to urinary tract infections and vascular infections.

In one embodiment, a composition comprises an antibiofilm composition comprising two or more antimicrobial agents selected from the group consisting of DispersinB™, 5-Fluorouracil, Deoxyribonuclease I and Proteinase K or active fragments thereof. An amount of DispersinB™ included in a composition is preferably between about 0.5 and about 500 μg/ml and more preferably between about 20 and about 200 μg/ml. An amount of FU included in a composition is preferably between about 5 and about 500 μg/ml and more preferably between about 10 and about 250 μg/ml. An amount of DNase I included in a composition is preferably between about 10 and about 1000 μg/ml and more preferably about 100 and about 500 μg/ml. An amount of PK included in a composition is preferably between about 10 and about 1000 μg/ml and more preferably about 100 and 500 μg/ml. The higher end of this range can be used to prepare a concentrated product which may be diluted prior to use.

Higher concentrations of a compound can be used for certain applications depending on targeted bacteria and a device to be treated. Suitable working concentrations can easily be determined using known methods.

In an embodiment of the present invention, wound dressings including but not limited to sponges or gauzes can be impregnated with two or more of the isolated DispersinB™, 5-Fluorouracil, Deoxyribonuclease I and Proteinase K, or active fragments or variants thereof to prevent or inhibit bacterial or fungal attachment and reduce the risk of wound infections. Similarly, catheter shields as well as other materials used to cover a catheter insertion sites can be coated or impregnated with two or more of DispersinB™, 5-Fluorouracil, Deoxyribonuclease I and Proteinase K protein, or active fragments or variants thereof to inhibit bacterial or fungal biofilm attachment thereto. Adhesive drapes used to prevent wound infection during high risk surgeries can be impregnated with the isolated protein or active fragment or variant thereof as well. Additional medical devices which can be coated with two or more of DispersinB™, 5-Fluorouracil, Deoxyribonuclease I and Proteinase K protein or active fragments or variants thereof include, but are not limited to, central venous catheters, intravascular catheters, urinary catheters, Hickman catheters, peritoneal dialysis catheters, endotracheal catheters, mechanical heart valves, cardiac pacemakers, arteriovenous shunts, schleral buckles, prosthetic joints, tympanostomy tubes, tracheostomy tubes, voice prosthetics penile prosthetics, artificial urinary sphincters, synthetic pubovaginal slings, surgical sutures, bone anchors, bone screws, intraocular lenses, contact lenses, intrauterine devices, aortofemoral grafts and vascular grafts. Exemplary solutions for impregnating gauzes or sponges, catheter shields and adhesive drapes or coating catheter shields and other medical devices include, but are not limited to, phosphate buffered saline (pH approximately 7.5) and bicarbonate buffer (pH approximately 9.0). In yet another embodiment, any two or more of an isolated DispersinB™, 5-Fluorouracil, Deoxyribonuclease I and Proteinase K protein, or active fragments or variants thereof can be incorporated in a liquid disinfecting solution. Such solutions may further comprise antimicrobials or antifungals such as alcohol, providone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok® connectors, needleless connectors and hubs as well as other implantable devices. These solutions can also be used to coat or disinfect surgical instruments including, but not limited to, clamps, forceps, scissors, skin hooks, tubing, needles, retractors, scalers, drills, chisels, rasps and saws. In a preferred embodiment, the composition comprising any two or more of DispersinB™, 5-Fluorouracil, Deoxyribonuclease I and Proteinase K, active fragments, or a variants thereof, is used to coat a medical device, such as a catheter. Alternatively, the composition comprising an antibiofilm composition comprising two or more antimicrobial agents selected from the group consisting of DispersinB™, 5-Fluorouracil, Deoxyribonuclease I and Proteinase K, active fragments or a variants thereof, can be incorporated into the medical device as it is being made, for example, through an extrusion process. Compositions of the invention can be prepared using known methods. Generally, components are dissolved in a suitable solvent, such as water, glycerol, organic acids, and other suitable solvents Compositions of the invention useful for the treatment of devices may include any number of well known active components and base materials. Such compositions may further comprise ingredients such as, but not limited to: suitable solvents such as water; antibiotics such antibacterials and antifungals; binding, bonding, or coupling agent, cross-linking agent; or a pH adjuster.

Compositions of the invention useful for the treatment of devices may further comprise additional antimicrobial ingredients such as bis-phenols, biguanides, anilides, diamidines, halogen-releasing agents, metallic ions, chelating agents, cationic peptides/polypeptides, N-substituted maleimides, photosensitive drugs, and quaternary ammonium compounds. Examples of bis-phenols useful for preparing compositions of the present invention include, but are not limited to, triclosan and hexachlorophene. Examples of biguanides useful for preparing compositions of the present invention include, but are not limited to, chlorhexidine, chlorhexidine salts, alexidine and polymeric biguanides. Examples of anilides useful for preparing compositions of the present invention include, but are not limited to, triclocarban. Examples of diamidines useful for preparing compositions of the present invention include, but are not limited to, propamidine and dibromopropamidine. Examples of halogen-releasing agents useful for preparing compositions of the present invention include, but are not limited to, iodine compounds, silver compounds, silver nanoparticles and halophenols. Examples of metallic ions useful for preparing compositions of the present invention include, but are not limited to, gallium and other related metal derivatives. Examples of chelating agents useful for preparing compositions of the present invention include, but are not limited to, lactoferrin, ovotransferrin, serotransferrin, EDTA and EGTA. Examples of cationic peptides/polypeptides useful for preparing compositions of the present invention include, but are not limited to, protamine sulfate, lyzozyme and polylysine. Examples of N-maleimides useful for preparing compositions of the present invention include, but are not limited: to N-ethylmaleimide (NEM), 5,5-dithiobis-(2-nitrobenzoic acid) (DTNB), N-phenylmaleimide (PheM), N-(1-pyrenyl) maleimide (PyrM), naphthalene-1,5-dimaleimide (NDM), N,N'-(1,2-phenylene)dimaleimide (oPDM), N,N'-1,4-phenylene dimaleimide (pPDM), N,N'-1,3-phenylene dimaleimide (mPDM), and 1,1-(methylenedi-4,1-phenylene)bismaleimide (BM). Examples of quaternary ammonium compounds useful for preparing compositions of the present invention include, but are not limited to benzalkonium chloride, tridodecyl methyl ammonium chloride, cetrimide and didecyl dimethyl ammonium chloride. Examples of photosensitive drugs useful for preparing compositions of the present invention include, but not limited to, methylene blue, nuclear Fast Red, delta-aminolaevulinic acid, phenothiazine chloride, tetra(N-methyl-4-pyridyl)porphine tetratosylate salt (TMPyP), toluidine blue 0 (TBO), methylene blue trihydrate (MB), Photolon, protoporhyrin PPIX, merocyanine 540, photofrin, aluminum phthalocyanine chloride.

Other possible components of the composition include, but are not limited to, buffer solutions, phosphate buffered saline, saline, polyvinyl, polyethylene, polyurethane, polypropylene, silicone (e.g., silicone lassoers and silicone adhesives), polycarboxylic acids, (e.g., polyacrylic acid, polymethacrylic acid, polymaleic acid, poly-(maleic acid monoester), polyaspartic acid, polyglutamic acid, aginic acid or pectimic acid), polycarboxylic acid anhydrides (e.g., polymaleic anhydride, polymethacrylic anhydride or polyacrylic acid anhydride), polyamines, polyamine ions (e.g., polyethylene imine, polyvinylamine, polylysine, poly-(dialkylamineoethyl methacrylate), poly-(dialkylaminomethyl styrene) or poly-(vinylpyridine), polyammonium ions (e.g., poly-(2-methacryloxyethyl trialkyl ammonium ion), poly-(vinylbenzyl trialkyl ammonium ions), poly-(N,N-alkylypyridinium ion) or poly-(dialkyloctamethylene ammonium ion) and polysulfonates (e.g. poly-(vinyl sulfonate) or poly-(styrene sulfonate), collodion, nylon, rubber, plastic, polyesters, Dacron™ (polyethylene tetraphthalate), Teflon™ (polytetrafluoroethylene), latex, and derivatives thereof, elastomers and Dacron (sealed with gelatin, collagen or albumin, cyanoacrylates, methacrylates, papers with porous barrier films, adhesives, e.g., hot melt adhesives, solvent based adhesives, and adhesive hydrogels, fabrics, and crosslinked and non-crosslinked hydrogels, and any other polymeric materials which facilitate dispersion of the active components and adhesion of the biofilm penetrating coating to at least one surface of the medical device. Linear copolymers, cross-linked copolymers, graft polymers, and block polymers, containing monomers as constituents of the above-exemplified polymers may also be used.

Examples of biofilm embedded bacteria that may be inhibited using compositions according to the invention include gram-negative bacteria such as, but not limited to: *Escherichia coli, Proteus mirabilis, Klebsiella pneumoniae, Pseudomonas aeruginosa, Klebsiella oxytoca, Providentia stuartii,* or *Serratia marcescens* and gram-positive bacteria such as, but not limited to: *Enterococcus faecalis*, Vancomycin Resistant Enterococci (VRE), *Streptococcus viridans, Staphylococcus epidermidis*, and *Staphylococcus aureus* or *Staphylococcus saprophyticus*. These bacteria are commonly found associated with medical devices including catheters.

Compositions according to the invention can also be used to inhibit the growth and proliferation of biofilm embedded fungus such as *Candida albicans, Candida parapsilosis*, and *Candida utilis*. In another aspect, the present invention provides a method of preparing a device comprising treating at least one surface of the device with an effective amount of an antibiofilm composition comprising two or more antimicrobial agents selected from the group consisting of DispersinB™, 5-Fluorouracil, Deoxyribonuclease I and Proteinase K, active fragments or variants thereof, according to the invention.

The term "effective" refers to a sufficient amount of active components to substantially prevent growth or proliferation of biofilm embedded microorganisms on at least one surface of a medical device coated with an embodied composition; and as a sufficient amount of the active components to substantially penetrate, or break-up, a biofilm on at least one surface of a medical device, thereby facilitating access of active components, antimicrobial agents, and/or antifungal agents to microorganisms embedded in a biofilm, and thus, removal of substantially all microorganisms from at least one surface of a medical device treated with a solution of an embodied composition. An amount will vary for each active component and upon known factors such as pharmaceutical characteristics; type of medical device; degree of biofilm embedded microorganism contamination; and use and length of use.

Examples of devices that can be treated using the compositions of the invention include medical devices such as tubing and other medical devices, such as catheters, pacemakers, prosthetic heart valves, prosthetic joints, voice prostheses, contact lenses, and intrauterine devices.

Medical devices include disposable or permanent or indwelling catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts heart valves, heart assist devices (e.g., left ventricular assist devices), pacemaker capsules, incontinence devices, penile implants, endotracheal tubes, small or temporary joint replacements, urinary dilator, cannulas, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, wound dressings, orthopedic implants, and any other device used in the medical field.

Medical devices also include any device which may be inserted or implanted into a human being or other animal, or placed at the insertion or implantation site such as the skin near the insertion or implantation site, and which include at least one surface which is susceptible to colonization by biofilm embedded microorganisms.

Medical devices for the present invention include surfaces of equipment in operating rooms, emergency rooms, hospital rooms, clinics, and bathrooms.

Implantable medical devices include orthopedic implants, which may be inspected for contamination or infection by biofilm embedded microorganisms using endoscopy. Insertable medical devices include catheters and shunts, which can be inspected without invasive techniques such as endoscopy.

Medical devices may be formed of any suitable metallic materials or non-metallic materials. Examples of metallic materials include, but are not limited to, titanium, and stainless steel, and derivatives or combinations thereof. Examples of non-metallic materials include, but are not limited to, thermoplastic or polymeric materials such as rubber, plastic, polyesters, polyethylene, polyurethane, silicone, Gortex™ (polytetrafluoroethylene), Dacron™ (polyethylene tetraphthalate), Teflon™ (polytetrafluoroethylene), latex, elastomers, and Dacron™ sealed with gelatin, collagen, or albumin, and derivatives or combinations thereof.

In a preferred embodiment, the method of treating at least one surface of a medical device comprises contacting a medical device with a composition according to the invention. As used herein, the term "contacting" includes, but is not limited to: coating, spraying, soaking, rinsing, flushing, submerging, and washing. A medical device is contacted with a composition for a period of time sufficient to remove substantially all biofilm embedded microorganisms from a treated surface of a medical device.

In a more preferred embodiment, a medical device is submerged in a composition for at least 5 minutes. Alternatively, a medical device may be flushed with a composition. In the case of a medical device being tubing, such as dental drain tubing, a composition may be poured into dental drain tubing and both ends of the tubing clamped such that the composition is retained within the lumen of the tubing. The tubing is then allowed to remain filled with the composition for a period of time sufficient to remove substantially all of the microorganisms from at least one surface of the medical device, generally, for at least about 1 minute to about 48 hours. Alternatively, tubing may be flushed by pouring a composition into the lumen of the tubing for an amount of time sufficient to prevent substantial growth of all biofilm embedded microorganisms. Concentrations of active components in a composition may vary as desired or necessary to decrease the amount of time the composition is in contact with a medical device.

In another embodiment of a method for treating a surface of a device, a composition of the invention may also include an organic solvent, a medical device material penetrating agent, or adding an alkalinizing agent to the composition, to enhance reactivity of a surface of the medical device with the composition. An organic solvent, medical device material penetrating agent, and/or alkalinizing agent are those which preferably facilitate adhesion of a composition to at least one surface of a medical device.

Another aspect provides a method of coating a composition of the invention onto at least one surface of a device. Preferably, the device is a medical device. Broadly, a method for coating a medical device includes the steps of providing a medical device; providing or forming a composition coating; and applying the composition coating to at least one surface of the medical device in an amount sufficient to substantially prevent growth or proliferation of biofilm embedded microorganisms on at least one surface of the medical device. In one specific embodiment, a method for coating a medical device includes the steps of forming a composition of the invention of an effective concentration for activating an active component, thereby substantially preventing growth or proliferation of microorganisms on at least one surface of the medical device, wherein the composition of the invention is formed by combining an active component and a base material. At least one surface of a medical device is then contacted with a composition of the invention under conditions wherein the composition of the invention covers at least one surface of the medical device. The term "contacting" further includes, but is not limited to: impregnating, compounding, mixing, integrating, coating, spraying and dipping.

In another embodiment of a method for coating a medical device, a composition coating is preferably formed by combining an active component and a base material at room temperature and mixing the composition for a time sufficient to evenly disperse active agents in the composition prior to applying the composition to a surface of the device. A medical device may be contacted with a composition for a period of time sufficient for a composition to adhere to at least one surface of the device. After a composition is applied to a surface of a device, it is allowed to dry.

A device is preferably placed in contact with a composition by dipping the medical device in the composition for a period of time ranging from about 30 seconds to about 180 minutes at a temperature ranging from about 25° C. to about 60° C. Preferably, a device is placed in contact with a composition by dipping the medical device in the composition for about 60 minutes at a temperature of about 37° C. A device is removed from a composition and then allowed to dry. A medical device may be placed in an oven or other heated environment for a period of time sufficient for a composition to dry.

Although one layer, or coating, of a composition is believed to provide a desired composition coating, multiple layers are preferred. Multiple layers of a composition are preferably applied to at least one surface of a medical device by repeating steps discussed above. Preferably, a medical device is contacted with a composition three times, allowing the composition to dry on at least one surface of the medical device prior to contacting the medical device with the composition for each subsequent layer. Thus, a medical device preferably includes three coats, or layers, of a composition on at least one surface of the medical device.

In another embodiment, a method for coating medical devices with a composition coating includes the steps of forming a composition coating of an effective concentration to substantially prevent the growth or proliferation of biofilm embedded microorganisms on at least one surface of a medical device by dissolving an active component in an organic solvent, combining a medical device material penetrating agent to the active component(s) and organic solvent, and combining an alkalinizing agent to improve reactivity of the material of the medical device. A composition is then heated to a temperature ranging from about 30° C. to about 60° C. to enhance adherence of a composition coating to at least one surface of the device. A composition coating is applied to at least one surface of a medical device, preferably by contacting the composition coating to the at least one surface of the medical device for a sufficient period of time for the composition coating to adhere to at least one surface of the medical device. A medical device is removed from a composition coating and allowed to dry, preferably, for at least 18 hours at room temperature. A medical device may then be rinsed with a liquid, such as water and allowed to dry for at least 2 hours, and preferably 4 hours, before being sterilized. To facilitate drying of a composition of the invention onto a surface of a medical device, a medical device may be placed into a heated environment such as an oven.

In another aspect, the invention provides a method of incorporating a composition according to the invention into a device. Preferably, a device is a medical device and a composition is incorporated into a material forming the medical device during formation of the medical device. For example, a composition may be combined with a material forming the medical device, e.g., silicone, polyurethane, polyethylene, Gortex™ (polytetrafluoroethylene), Dacron™ (polyethylene tetraphthalate), and Teflon™ (polytetrafluoroethylene), and/or polypropylene, and extruded with the material forming the medical device, thereby incorporating the composition into material forming the medical device. In this embodiment, the composition may be incorporated in a septum or adhesive, which is placed at the medical device insertion or implantation site. One example of a medical device having a composition incorporated into the material forming the medical device in accordance with this embodiment is a catheter insertion seal having an adhesive layer described below in greater detail. Another example of a medical device having a composition incorporated into the material is an adhesive. A composition of the invention can be integrated into an adhesive, such as tape, thereby providing an adhesive, which may prevent growth or proliferation of biofilm embedded microorganisms on at least one surface of the adhesive.

EXAMPLES

Example 1

Effect of DispersinB™ and DNase I on *Staphylococcus epidermidis* Biofilm Formation An in vitro microplate assay was performed to determine the effect of DispersinB™ and DNase I on the growth and biofilm formation of *S. epidermidis*. An overnight culture of *S. epidermidis* in Tryptic Soy Broth (TSB) was used as inoculum. *S. epidermidis* biofilm was grown in TSB in a 96-well microtiterplate in the absence and presence of each enzyme (DispersinB™-1 µg/ml or DNase I-25 µg/ml) separately and together (DispersinB™+DNase I). The plate was incubated at 37° C. for 24 hours (h). Growth of planktonic cells based on the absorbance at 600 nm was determined using Labsystems Multiskan Ascent microplate reader. Biofilm was measured by discarding the medium; rinsing the wells with water (three times), and staining bound cells with crystal violet. The dye was solubilized with 33% acetic acid, and absorbance at 630 nm was determined using a microtiter plate reader. For each experiment, background staining was corrected by subtracting the crystal violet bound to uninoculated control. The combination of DispersinB™ and DNase I provided enhanced inhibition of *S. epidermidis* biofilm as compared to the enzymes alone (FIG. 1).

Example 2

Figure 2:
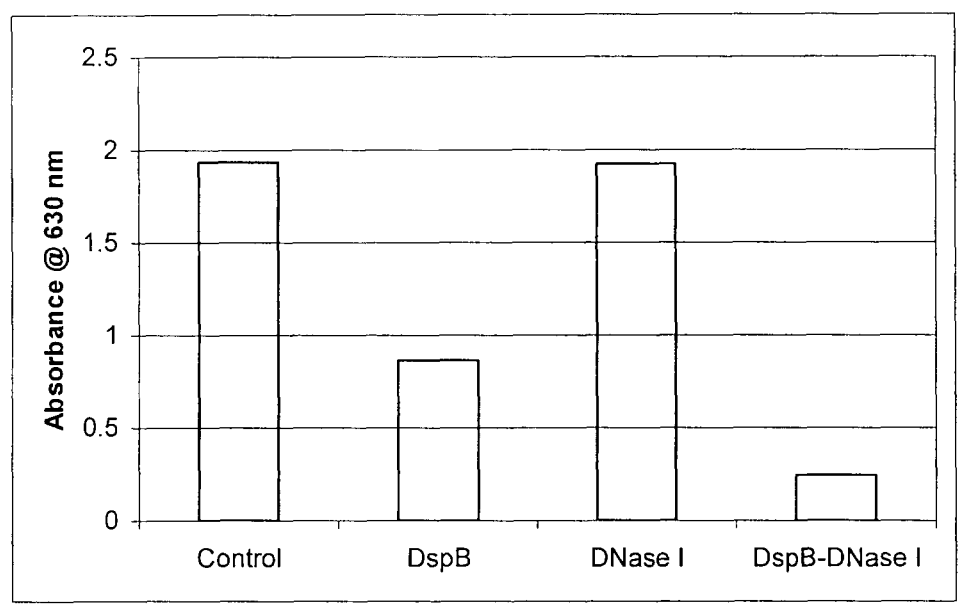
FIG. 2 is a bar graph showing the effect of DispersinB™ (10 µg/ml), and DNaseI (25 µg/ml) on dispersal of *Staphylococcus epidermis* biofilm.

Effect of DispersinB™ and DNase I on *Staphylococcus epidermidis* Biofilm Dispersal An in vitro microplate assay was performed to determine the effect of DispersinB™ and DNase I on the dispersal of *S. epidermidis* biofilm. *S. epidermidis* biofilm in absence of enzyme was grown at 37° C. for 24 h as explained in Example 1. The planktonic cells were discarded and biofilm was treated with water (control), and DispersinB™ (10 µg/ml), DNase I (25 µg/ml) alone and in combination (DispersinB™+DNase I) for 2 h at 37° C. Biofilm was measured as explained in Example 1. The combination of DispersinB™ and DNase I provided enhanced dispersion of *S. epidermidis* biofilm as compared to the enzymes alone (FIG. 2).

Example 3

Figure 3:
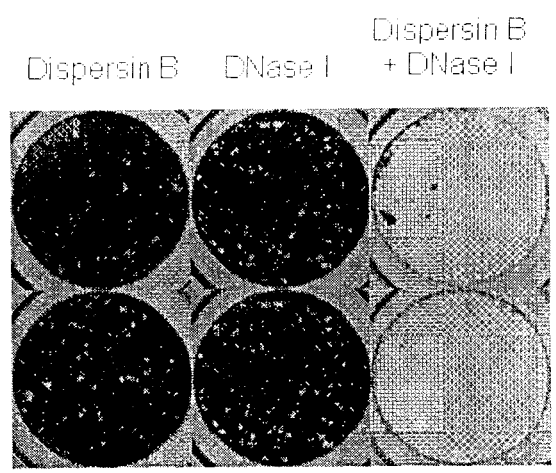
FIG. 3 shows the biofilm dispersal of *Aggregatibacter actinomycetemcomitans* with DispersinB™ (20 ug/ml) and DNase1 (100 µg/ml). Biofilms were stained with crystal violet.

Effect of DispersinB™ and DNase I on *Aggregatibacter actinomycetemcomitans* Biofilm Dispersal An in vitro microplate assay was performed to determine the effect of DispersinB™ and DNase I on the dispersal of *A. actinomycetemcomitans* biofilm. *A. actinomycetemcomitans* biofilm in the absence of enzyme was grown at 37° C. for 24 h as explained in Example 1. The planktonic cells were discarded and biofilm was treated with DispersinB™ (20 µg/ml), DNase I (100 µg/ml) alone and in combination (DispersinB™+DNase I) for 1 h at 37° C. Biofilms were then rinsed with water and stained with crystal violet. Duplicate wells are shown in FIG. 3. The combination of DispersinB™ and DNase I provided enhanced dispersion of *A. actinomycetemcomitans* biofilm as compared to the enzymes alone.

Example 4

Figure 4:
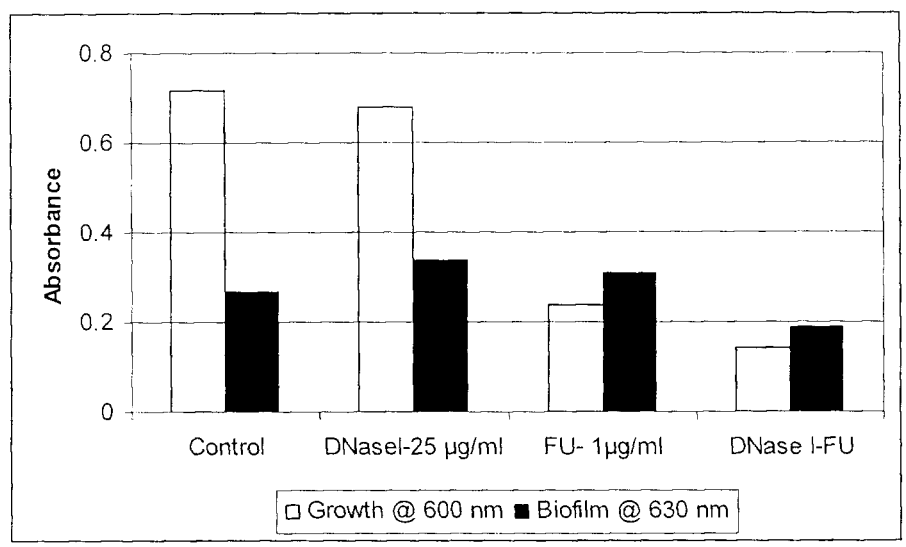
FIG. 4 shows the effect of DNase I (1-25 µg/ml) and FU (1 µg/ml) on growth and biofilm formation of *Staphylococcus aureus*.

Effect of DNase 1 and 5-Fluorouracil (FU) on *Staphylococcus aureus* Biofilm Formation An in vitro microplate assay was performed to determine the effect of DNase 1 and 5-fluorouracil on the growth and biofilm formation of *S. aureus*. An overnight culture of *S. aureus* in Tryptic Soy Broth (TSB) was used as inoculum. *S. aureus* biofilm was grown as described in example 1 in the presence of DNase I-25 FU-1 µg/ml alone and together (DNase I+FU). The combination of DNase I and FU provided enhanced inhibition of *S. aureus* biofilm as compared to the compounds alone (FIG. 4).

Example 5

Enhancing Effect of DNase I (100 µg/ml) on the Sensitivity of *Pseudomonas aeruginosa* Biofilm to 5-Fluorouracil (FU)

Figure 5:
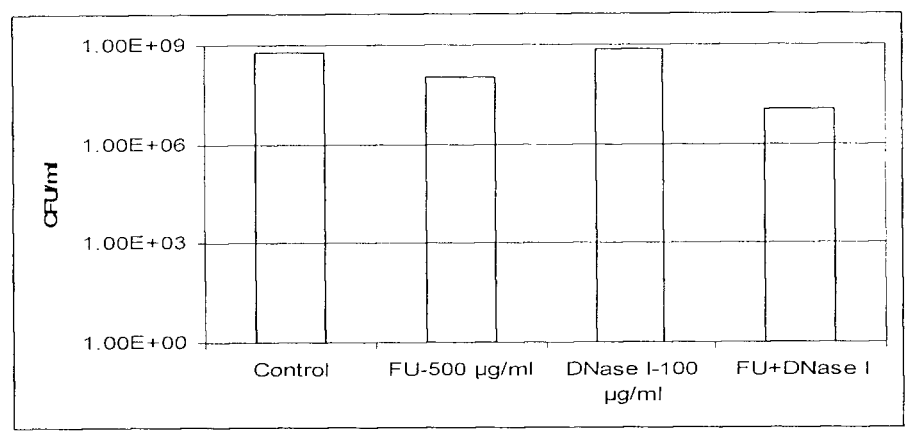
FIG. 5 shows the enhancing effect of DNase I (100 µg/ml) on the sensitivity of *Pseudomonas aeruginosa* biofilm to FU (500 µg/ml).

An in vitro biofilm dispersal assay was performed to determine the effect of DNase I (100 mg/ml) and 5-fluorouracil (FU-500 µg/ml) on the dispersal of *P. aeruginosa* biofilm. *P. aeruginosa* biofilm in absence of enzyme was grown in 1.5 ml polypropylene microcentrifuge tubes. Tubes were filled with 200 µl of inoculum (diluted 1:100 in fresh TSB). After 16 h the broth was aspirated and replaced with fresh broth containing 100 µg/ml of DNase 1 and 500 µg/ml FU alone and in combination (DNase I+FU). After 3 h the cells were pelleted and rinsed with saline. Cell pellets were resuspended in 200 µl of saline. Tubes were vortexed and number of colony forming units (CFUs/ml) was determined by plating serial dilutions on tryptic soy agar (TSA). DNase I in combination with FU increased the sensitivity of *P. aeruginosa* biofilm to FU (FIG. 5). Thus, the DNase I and FU combination had enhanced effect on killing biofilm-embedded *P. aeruginosa*.

Example 6

Figure 6:
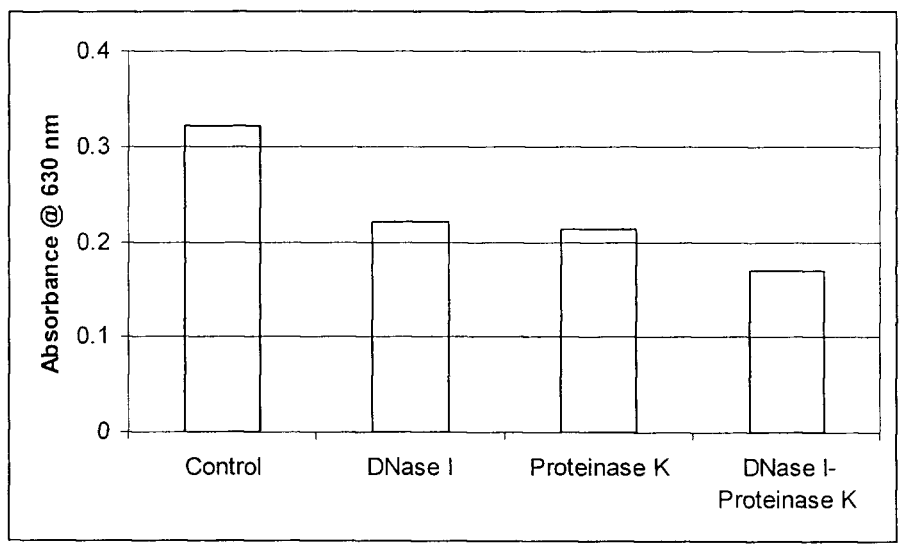
FIG. 6 shows the effect of DNase I (500 µg/ml) and PK (100 µg/ml) alone and in combination on dispersal of *Burkholderia cepacia* biofilm.

Effect of DNase I and Proteinase K Alone and in Combination on Dispersal of *Burkholderia cepacia* Biofilm An in vitro microplate assay was performed to determine the effect of DNase I and proteinase K on the dispersal of *B. cepacia* biofilm. *B. cepacia* biofilm in absence of enzyme was grown at 37° C. for 16-18 h as explained in Example 1. The planktonic cells were discarded and biofilm was treated with DNase I (500 µg/ml) and proteinase K (100 µg/ml) alone for 3 h at 37° C. For the combination of DNase I and proteinase K, the biofilm was first treated with DNase I alone for 90 min and then with proteinase K for 90 min at 37° C. Biofilms were then rinsed with water and stained with crystal violet. DNase I in combination with proteinase K enhanced the sensitivity of *B. cepacia* biofilm to proteinase K (FIG. 6).

Example 7

Antimicrobial Activity of 5-Fluorouracil Against Cystic Fibrosis-Associated Pathogens The antimicrobial activity of 5-fluorouracil (FU) was studied by determining minimal inhibitory concentrations (MIC) in a 96 well microtiter plate. Briefly, serial two-fold dilutions of FU were performed in TSB. A suspension of each microorganism from Table 1 was added to wells at a concentration of $5 \times 10^5$ CFU/mL, and the microtiter plates were incubated at 37° C. The MIC was defined, as the lowest concentration of an antimicrobial required for total inhibition of a test microorganism at 37° C. 5-Fluorouracil was active against all the pathogens tested (Table 1).

TABLE 1

MIC of 5-Fluorouracil against cystic fibrosis associated pathogens

| Pathogen | MIC (µg/ml) |
|---|---|
| *Staphylococcus aureus* | 25 |
| *Pseudomonas aeruginosa* | 31.25 |
| *Burkholderia cepacia* | 62.5 |

Example 8

Effect of DispersinB™ and DNase I on *Staphylococcus aureus* Biofilm Formation

Figure 7:
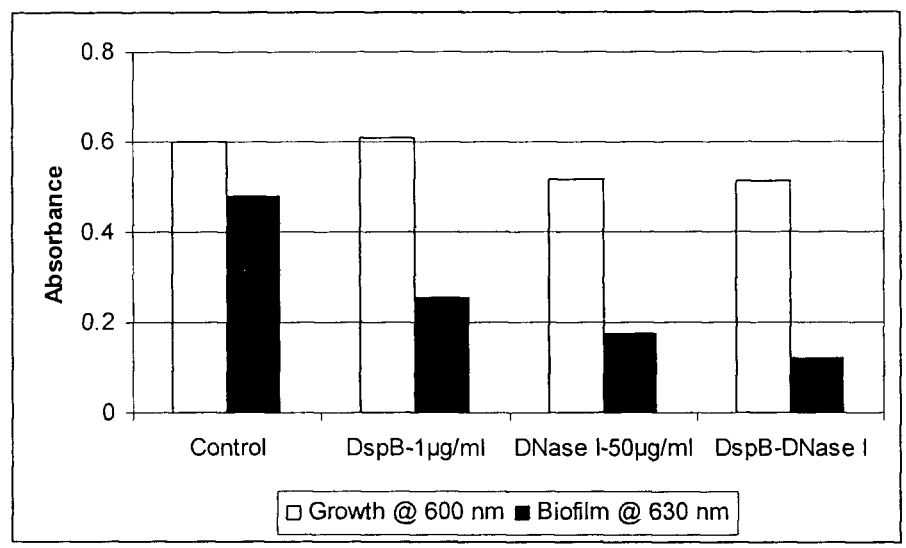
FIG. 7 shows the effect of DispersinB™ (1 µg/ml) and DNase I (50 µg/ml) on growth and biofilm formation of *Staphylococcus aureus*.

An in vitro microplate assay was performed to determine the effect of DispersinB™ and DNase I on the growth and biofilm formation of *S. aureus*. An overnight culture of *S. aureus* in Tryptic Soy Broth (TSB) was used as inoculum. *S. aureus* biofilm was grown as described in example 1 in the presence of DispersinB™-1 µg/ml, DNase I-50 µg/ml alone and together (DispersinB™+DNase I). The combination of DispersinB™ and DNase I enhanced the inhibition of *S. aureus* biofilm (FIG. 7).

Example 9

Figure 8:
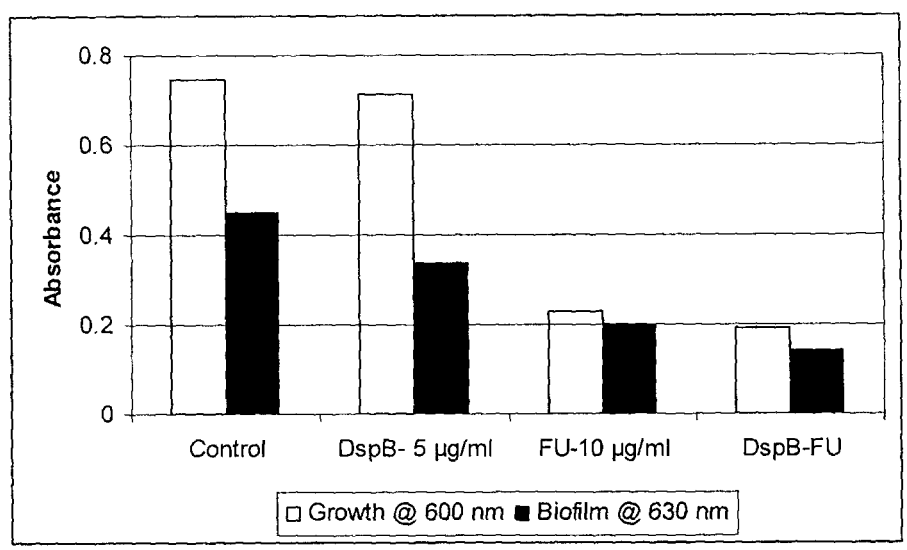
FIG. 8 shows the effect of DispersinB™ (5 µg/ml) and FU (10 µg/ml) on growth and biofilm formation of *Staphylococcus aureus*.

Effect of DispersinB™ and 5-Fluorouracil (FU) on *Staphylococcus aureus* Biofilm Formation An in vitro microplate assay was performed to determine the effect of DispersinB™ and FU on the growth and biofilm formation of *S. aureus*. An overnight culture of *S. aureus* in Tryptic Soy Broth (TSB) was used as inoculum. *S. aureus* biofilm was grown as described in example 1 in the presence of DispersinB™ (5 µg/ml) and FU (10 ng/ml) alone and together (DispersinB™+FU). The combination of DispersinB and FU provided enhanced inhibition of *S. aureus* biofilm (FIG. 8).

Example 10

Figure 9:
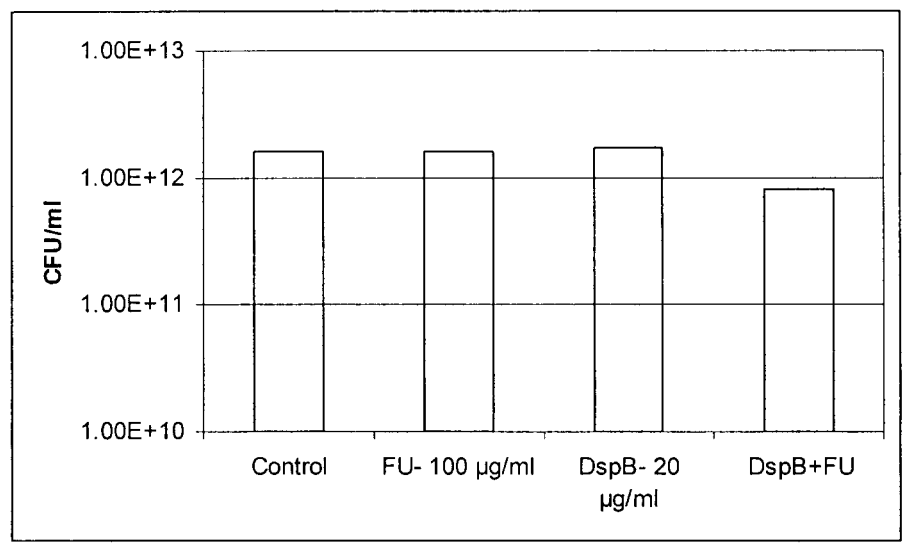
FIG. 9 shows the enhancing effect of DispersinB™ (5 µg/ml) on the sensitivity of *Staphylococcus epidermidis* biofilm to FU (100 µg/ml).

Enhancing Effect of DispersinB™ on the Sensitivity of Biofilm-Embedded *Staphylococcus epidermidis* to 5-Fluorouracil An in vitro biofilm dispersal assay was performed to determine the effect of DispersinB™ on the sensitivity of biofilm-embedded *S. epidermidis* to 5-fluorouracil (FU). *S. epidermidis* biofilm grown in 1.5 ml polypropylene microcentrifuge tubes was rinsed with 200 µl of fresh medium and then treated with 200 µl medium containing 100 µg/ml of 5-FU and/or 20 µg/ml of DispersinB™. Biofilm detachment and plating biofilm embedded cells were performed as described in Example 5. When DispersinB™ was used in combination with FU, there was increased sensitivity of biofilm-embedded *S. epidermidis* to FU (FIG. 9). Thus, the DispersinB™ and 5-FU combination had an enhanced inhibitory effect on biofilm-embedded *S. epidermidis*.

Example 11

Figure 10:
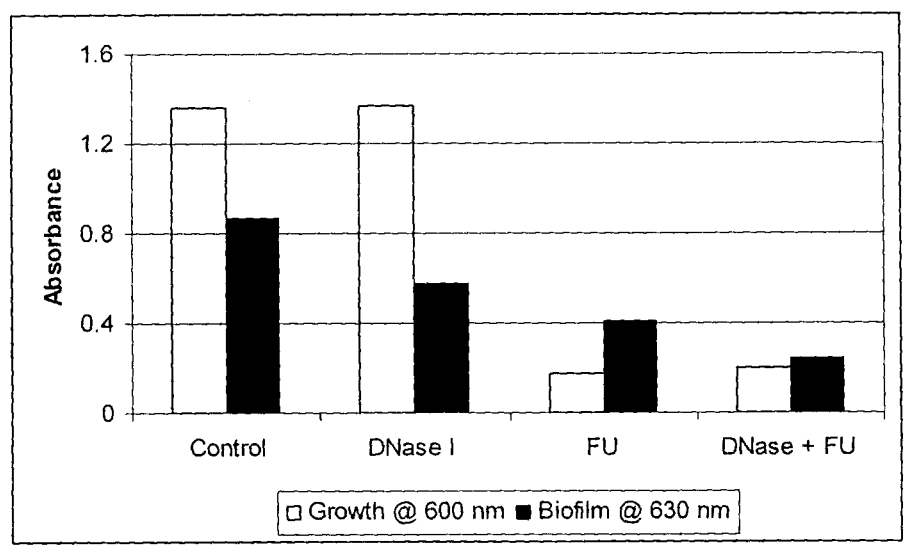
FIG. 10 shows the effect of DNase I (50 µg/ml) and FU (10 µg/ml) on growth and biofilm formation of *Pseudomonas aeruginosa*.

Effect of DNase 1 and 5-Fluorouracil (FU) on *Pseudomonas aeruginosa* Biofilm Formation An in vitro microplate assay was performed to determine the effect of DNase I and 5-fluorouracil (FU) on the growth and biofilm formation of *P. aeruginosa*. An overnight culture of *P. aeruginosa* in Tryptic Soy Broth (TSB) was used as inoculum. *P. aeruginosa* biofilm was grown in colony forming antigen (CFA) medium on a 96-well microtiterplate in the absence and presence of DNase I-50 µg/ml or FU (10 µg/ml) separately and together (DNase I+FU). The plate was incubated at 26° C. for 24 h. The planktonic growth and biofilm was estimated as described in Example 1. The combination of DNase I and FU showed significant enhancement in inhibiting *P. aeruginosa* biofilm as compared to compounds alone (FIG. 10).

Example 12

Figure 11:
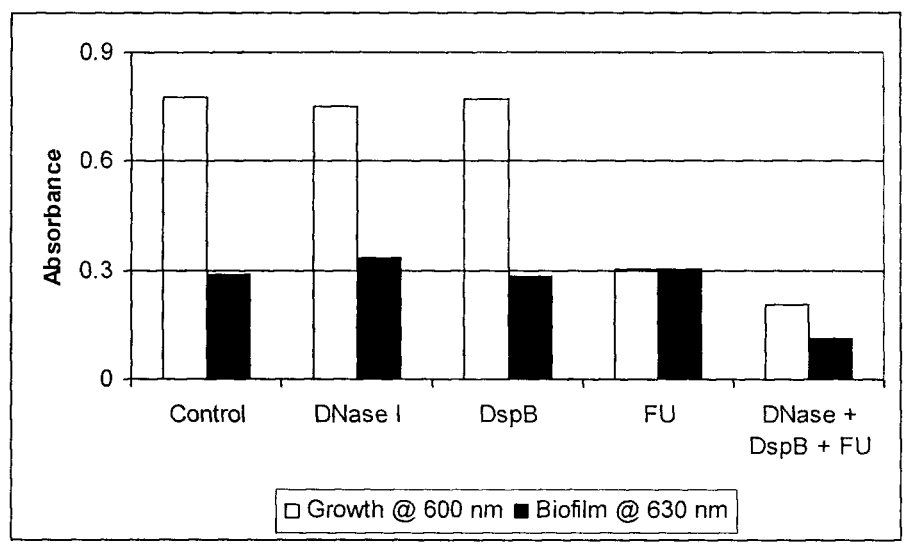
FIG. 11 show the effect of DNase I (25 µg/ml), DispersinB™ (5 µg/ml) and FU (10 µg/ml) on growth and biofilm formation of *Staphylococcus aureus*.

Effect of DNase I, DispersinB™ and 5-fluorouracil (FU) on *Staphylococcus aureus* Biofilm Formation An in vitro microplate assay was performed to determine the effect of DNase I, DispersinB™ and 5-fluorouracil (FU) on the growth and biofilm formation of *S. aureus*. An overnight culture of *S. aureus* in Tryptic Soy Broth (TSB) was used as inoculum. *S. aureus* biofilm was grown in TSB medium on a 96-well microtiterplate in the absence and presence of DNase I (25 µg/ml), DispersinB™ (5 µg/ml) or FU (10 µg/ml) separately and in combination (DNase I+DispersinB+FU). The plate was incubated at 37° C. for 24 h. The planktonic growth and biofilm was estimated as described in Example 1. The combination of DNase I, DispersinB™ and FU showed significant enhancement in inhibiting *S. aureus* biofilm than the compounds alone (FIG. 11).

Example 13

Figure 12:
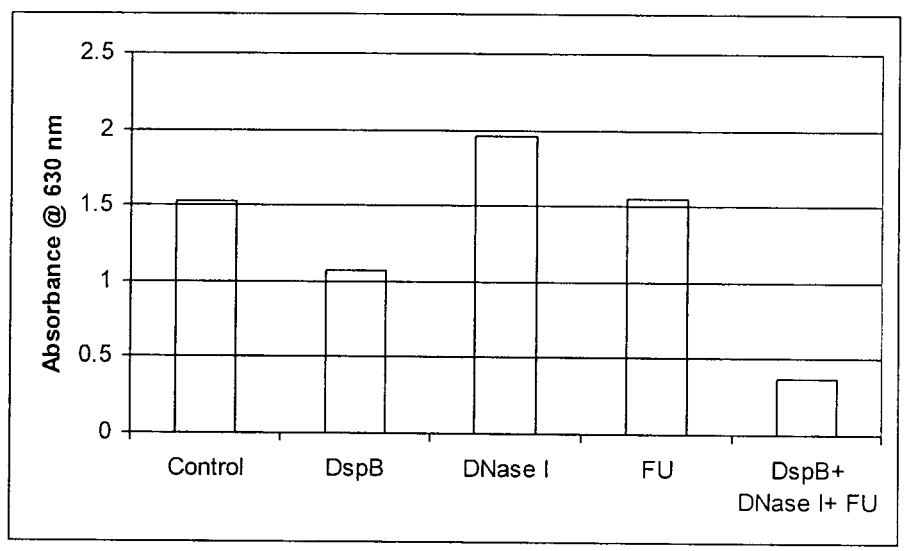
FIG. 12 shows the effect of DispersinB™ (10 µg/ml), DNase I (100 µg/ml) and FU (200 µg/ml) on *Staphylococcus epidermidids* biofilm dispersal.

Effect of DispersinB™, DNase I, and 5-Fluorouracil on *Staphylococcus epidermidis* Biofilm Dispersal An in vitro microplate assay was performed to determine the effect of DispersinB™ DNase I, and 5-fluorouracil (FU) on the dispersal of *S. epidermidis* biofilm. *S. epidermidis* biofilm in absence of enzyme was grown at 37° C. for 24 h as explained in Example 1. The planktonic cells were discarded and biofilm was treated with water (control), and DispersinB™ (10 µg/ml), DNase I (100 µg/ml), and FU (200 ng/ml) alone and in combination (DispersinB™+DNase I+FU) for 3 h at 37° C. Biofilm was measured as explained in Example 1. The combination of DispersinB™, DNase I and FU showed significant enhancement in dispersing *S. epidermidis* biofilm than the compounds alone (FIG. 12).

The invention claimed is:

1. A composition comprising: (a) Dispersin B®, or variant thereof; (b) 5-fluorouracil; (c) deoxyribonuclease I or an active fragment thereof.

2. The composition of claim 1 wherein the DispersinB® or variant thereof comprises an amino acid sequence selected from the group consisting of SEQ ID NO: 1 and SEQ ID NO: 4.

3. The composition of claim 1 further comprising an agent selected from the group consisting of: a binder, a wetting agent, an odor absorbing agent, a levelling agent, an adherent, a thickener, an antistatic agent, an optical brightening compound, an opacifier, a nucleating agent, an antioxidant, a UV stabilizer, a filler, a permanent press finish, a softener, a lubricant, a curing accelerator, an adhesive, a gum, a polysaccharide, an alginate, a synthetic polymeric compound, a gel, polyethylene glycol, a polyethylene glycol/ethanol gel, an antibiotic, and a natural polymeric compound.

4. The composition of claim 1 further comprising a compound selected from the group consisting of a buffer solution, a phosphate buffered saline, a saline, a polyvinyl, a polyethylene, a polyurethane, a polypropylene, a silicone (e.g., silicone lassoers and silicone adhesives), a polycarboxylic acids, (e.g., polyacrylic acid, polymethacrylic acid, polymaleic acid, a poly-(maleic acid monoester), a polyaspartic acid, a polyglutamic acid, aginic acid, pectimic acid, a polycarboxylic acid anhydride (e.g., polymaleic anhydride, polymethacrylic anhydride or polyacrylic acid anhydride), a polyamine, a polyamine ions (e.g., polyethylene imine, polyvinylamine, polylysine, a poly-(dialkylamineoethyl methacrylate), a poly-(dialkylaminiomethyl styrene), poly-(vinylpyridine), a polyammonium ion (e.g., poly-(2-methacryloxyethyl trialkyl ammonium ion), a poly-vinylbenzyl trialkyl ammonium ion, a poly-(N,N-alkylpyridinium ion), a poly-(dialkyloctamethylene ammonium ion), a polysulfonate (e.g. poly-(vinyl sulfonate) or poly-(styrene sulfonate), collodion, nylon, rubber, plastic, polyester, Dacron™ (polyethylene tetraphthalate), Teflon™ (polytetrafluoroethylene), latex and derivatives thereof, elastomers and Dacron (sealed with gelatine, collagen or albumin), cyanoacrylates, methacrylates, papers with porous barrier films, adhesives, e.g., hot melt adhesives, solvent based adhesives, adhesive hydrogels, fabrics, a quorum sensing inhibitor, RNAIII inhibitory peptide (RIP), a bis-phenol, a biguanide, an anilide, a diamidine, a halogen-releasing agent, a metallic ion, a chelating agent, a cationic peptides, a cationic polypeptides, an N-substituted maleimide, and a quaternary ammonium compounds, crosslinked hydrogels, and non-crosslinked hydrogels.

5. The composition of claim 1 wherein the composition comprises Dispersin B®, 5-fluorouracil, and deoxyribonuclease I.

6. The composition of claim 1 wherein the composition further comprises Proteinase K.

7. An ointment, gel, lotion, non-resorbably gauze/sponge dressing, hydrophilic wound dressing, occlusive wound dressing, hydrogel wound dressing, a burn dressing, or spray applicator comprising the composition of claim 1.

8. A wound care device comprising the composition of claim 1.

9. A device comprising the composition of claim 1.

10. The device of claim 9, wherein the device is a medical device selected from the group consisting of an indwelling catheter such as a central venous catheter, a peripheral intravenous catheter, an arterial catheter, a peritoneal catheter, a haemodialysis catheter, an umbilical catheter, a precutaneous nontunneled silicone catheter, a cuffed tunneled central venous catheter, an endotracheal tube, a subcutaneous central venous port, a urinary catheter, a peripheral intravenous catheter or a ventral venous catheter, a pacemaker, a prosthetic heart valve, a prosthetic joint, a voice prostheses, a contact lens, a shunt, a heart valve, a penile implant, a small or temporary joint replacement, a urinary dilator, a cannula, an elastomer, an intrauterine device, a catheter lock, a needle, a Leur-Lok® connector, a needleless connector, a clamp, a forcep, a scissor, a skin hook, a tubing, a needle, a retractor, a scaler, a drill, a chisel, a rasp, a surgical instrument, a dental instrument, a tube, an intravenous tube, a breathing tube, a dental water line, a dental drain tube, a feeding tube, a bandage, a wound dressing, an orthopaedic implant, a catheter shield, an adhesive drape, and a saw.

11. A method of preparing a device comprising incorporating, treating or coating at least one surface of the device with a composition of claim 1.

12. A method of inhibiting proliferation of biofilm-embedded microorganisms comprising administering a composition of claim 1.

13. The method of claim 12 wherein the biofilm-embedded microorganism is selected from the group consisting of *Aggregatibacter actinomycetemcomitans*, *Staphylococcus aureus*, *Burkholderia cepacia*, *Escherichia coli*, *Proteus mirabilis*, *Klebsiella pneumoniae*, *Pseudomonas aeruginosa*, *Klebsiella oxytoca*, *Providentia sturtii*, *Serratia marcescens*, *Enterococcus faecalis*, Vancomycin Resistant Enterococci (VRE), *Peptostreptococcus* spp., *Corynebacterium* spp., *Clostridium* spp., *Bacteriodes* spp., *Prevotella* spp., *Streptococcus pyogenes*, *Streptococcus viridians*, *Mirococcus* spp., Beta-hemolytic *streptococcus* (group C), Beta-hemolytic *streptococcus* (group B), *Bacillus* spp., *Porphyromonas* spp., *Enterobacteria cloacae*, *S. epidermis*, *S. aureus*, *Staphylococcus egalactiae*, *Staphlococcus saprophyticus*, *Candida albicans*, *Candida parapsilosis*, and *Candida utilis*.

14. A method of treating a disease-related infection caused by biofilms comprising administering a composition of claim 1.

15. The method of claim 14 wherein the disease is cystic fibrosis.

16. A method of treating a wound comprising administering a composition of claim 1.

17. The method of claim 16 wherein the wound is selected from the group consisting of a cutaneous abscess, a surgical wound, a sutured laceration, a contaminated laceration, a burn wound, a decubitous ulcer, a stasis ulcer, a leg ulcer, a foot ulcer, a venous ulcer, a diabetic ulcer, an ischemic ulcer, and a pressure ulcer.

18. A method of treating an oral infection or disease comprising administration of a composition of claim 1.

19. The method of claim 18 wherein the oral infection or disease is selected from the group consisting of dental caries; dental plaque; gingivitis; periodontal disease; mucosal infection; oral cancer; pharyngeal cancer; and precancerous legion.

20. A method of inhibiting proliferation of biofilm-embedded microorganisms comprising administering a composition of claim 2.

21. A method of treating a disease-related infection caused by biofilms comprising administering a composition of claim 2.

22. A method of treating a wound comprising administering a composition of claim 2.

23. A method of inhibiting proliferation of biofilm-embedded microorganisms comprising administering a composition of claim 5.

24. A method of treating a disease-related infection caused by biofilms comprising administering a composition of claim 5.

25. A method of treating a wound comprising administering a composition of claim 5.

* * * * *